(12) United States Patent
Zhang et al.

(10) Patent No.: US 7,419,808 B2
(45) Date of Patent: Sep. 2, 2008

(54) METHODS AND COMPOSITIONS FOR THE PRODUCTION OF ADENOVIRAL VECTORS

(75) Inventors: Shuyuan Zhang, Sugar Land, TX (US); Hai Pham, Houston, TX (US)

(73) Assignee: Introgen Therapeutics, Inc., Austin, TX (US)

( * ) Notice: Subject to any disclaimer, the term of this patent is extended or adjusted under 35 U.S.C. 154(b) by 0 days.

(21) Appl. No.: 11/079,986

(22) Filed: Mar. 15, 2005

(65) Prior Publication Data

US 2005/0158283 A1 Jul. 21, 2005

Related U.S. Application Data

(62) Division of application No. 10/439,278, filed on May 15, 2003, now abandoned.

(51) Int. Cl.
C12P 21/04 (2006.01)
A61K 39/00 (2006.01)
A61K 39/235 (2006.01)
C12N 13/00 (2006.01)
A61K 39/193 (2006.01)

(52) U.S. Cl. ............... 435/70.1; 424/184.1; 424/233.1; 435/173.9

(58) Field of Classification Search .................. None
See application file for complete search history.

(56) References Cited

U.S. PATENT DOCUMENTS

| | | | | |
|---|---|---|---|---|
| 3,962,424 | A | 6/1976 | Zygraich et al. | 424/202.1 |
| 4,352,883 | A | 10/1982 | Lim | 435/178 |
| 5,585,362 | A | 12/1996 | Wilson et al. | 514/44 |
| 5,670,488 | A | 9/1997 | Gregory et al. | 514/44 |
| 5,824,544 | A | 10/1998 | Armentano et al. | 435/320.1 |
| 5,932,210 | A | 8/1999 | Gregory et al. | 424/93.2 |
| 6,190,913 | B1 * | 2/2001 | Singh | 435/394 |
| 6,194,191 | B1 | 2/2001 | Zhang et al. | 435/239 |
| 6,355,622 | B1 | 3/2002 | Fisher | 514/44 |
| 6,544,788 | B2 * | 4/2003 | Singh | 435/383 |
| 7,125,706 | B2 * | 10/2006 | Zhang et al. | 435/235.1 |
| 2002/0177215 | A1 * | 11/2002 | Zhang et al. | 435/235.1 |
| 2002/0182723 | A1 | 12/2002 | Zhang et al. | 435/320.1 |
| 2004/0106184 | A1 * | 6/2004 | Senesac | 435/239 |
| 2004/0229335 | A1 * | 11/2004 | Zhang et al. | 435/235.1 |
| 2005/0089999 | A1 * | 4/2005 | Zhang et al. | 435/320.1 |
| 2005/0287657 | A1 * | 12/2005 | Blanche et al. | 435/239 |
| 2006/0275781 | A1 * | 12/2006 | Pham et al. | 435/6 |

FOREIGN PATENT DOCUMENTS

| | | |
|---|---|---|
| CN | 1244215 | 2/2000 |
| WO | WO 94/17178 | 8/1994 |
| WO | WO 98/00524 | 1/1998 |
| WO | WO 01/77304 | 10/2001 |

OTHER PUBLICATIONS

Clontech Laboratories, Inc. Adeno-X™ Rapid Titer Kit Protocol-at-a-Glance (PT3651-2), published Jan. 3, 2002, 1 page.*

Xie et al. Serum-Free Suspension Cultivation of PER.C6® Cells and Recombinant Adenovirus Production Under Different pH Conditions 2002, Biotechnology and Bioengineering, vol. 80 No. 5, pp. 571.*

Zhang et al. Production of Adenoviral Vectors for Gene Therapy in Suspension Serum Free Cultures. Introgen Therapeutics, Inc. Presentation Posted at Wave Biotech, LLC. [online] in Mar. 2003 [Retrived Oct. 20, 2006], Retrived from the Internet:<URL: http://www.wavebiotech.com/products/wave_bioreactor/literature.html>.*

Singh V., Disposable bioreactor for cell culture using wave-induced agitation, 1999, Cytotechnology, vol. 30, pp. 149-158.*

Product information page for Wave Bioreactor System20, Posted at Wave Biotech, LLC. [Retrived Aug. 11, 2007], Retrived from the Internet:<URL: http://http://www.wavebiotech.com/products/wave_bioreactor/system20/index.html#>.*

U.S. Appl. No. 60/406,591, filed Aug. 28, 2002, Senesac et al.

Aboud et al., "Rapid purification of extracellular and intracellular Moloney murine Leukemia virus," *Arch. Virol.*, 71:185-195, 1982.

Batra et al., "IκBα gene transfer is cytotoxic to squamous-cell lung cancer cells and sensitizes them to tumor necrosis factor-α-mediated cell death," *Am. J. Respir. Cell Mol. Biol.*, 21(2):238-245, 1999.

Berg et al., "High-level expression of secreted proteins from cells adapted to serum-free suspension culture," *Biotechniques*, 14(6):972-978, 1993.

Bett et al., "An efficient and flexible system for construction of adenovirus vectors with-insertions or deletions in early regions 1 and 3," *Proc. Natl. Acad. Sci.*, USA, 91:8802-8806, 1994.

Blackwell et al., "Retargeting to EGFR enhances adenovirus infection efficiency of squamous cell carcinoma," *Ach. Otolaryngol. Head. Neck Surg.*, 125(8):856-863, 1999.

Chillon et al., "Group D adenoviruses infect primary central nervous system cells more efficiently that those from group C," *J. Virol.*, 73(3):2537-2540, 1999.

Chroboczek et al., "The sequence of the genome of adenovirus type 5 and its comparison with the genome of adenovirus type 2," *Virology*, 186:280-285, 1992.

(Continued)

*Primary Examiner*—Bruce Campell
*Assistant Examiner*—Benjamin P Blumel
(74) *Attorney, Agent, or Firm*—Fulbright & Jaworski L.L.P.

(57) ABSTRACT

The present invention addresses the need to improve the yield of adenovirus when grown in cell culture systems. In particular, it has been demonstrated that for adenovirus, the use of infection temperatures lower than 37° C. in a cell culture system results in improved yields of adenovirus. In addition, it has been demonstrated that when host cells are grow in a bioreactor, initiating adenovirus infection by diluting the host cells with fresh media and adenovirus results in improved yield of adenovirus. Methods of adenoviral production and purification using infection temperatures less than 37° C. are disclosed. Methods of adenoviral production and purification wherein the host cells are grown in a bioreactor and adenovirus infection is initiated by diluting the host cells with fresh media and adenovirus are also disclosed.

62 Claims, 6 Drawing Sheets

OTHER PUBLICATIONS

Cristiano et al, "Viral and nonviral gene delivery vectors for cancer gene therapy," *Cancer Detect. Prev.*, 22(5):445-454, 1998.

Crooks et al., "Purification and analysis of infectious virions and native non-structural antigens from cells infected with tick-borne encephalitis virus," *J. Chromatogr.*, 502(1):59-68, 1990.

Dorai et al., "A recombinant defective adenoviral agent expressing anti-Bcl-2 ribozyme promotes apoptosis of Bcl-2-expressing human prostate cancer cells," *Int. J. Cancer*, 82(6):846-852, 1999.

Engelhardt et al., "Ablation of E2A in recombinant adenoviruses improves transgene persistence and decreased inflammatory response in mouse liver," *PNAS* 91:6196-6200, 1994.

Fathallah-Shaykh et al., "Gene Transfer of IFN-γ into Established Brain Tumors Represses Growth by Antiangiogenesis," *J of Immunology*, 164:217-222, 2000.

Feldman et al., "Perspective of arterial gene therapy for the prevention of restenosis," *Cardiovasc. Res.*, 32(2):194-207, 1996.

Garnier et al., "Scale-up of the adenovirus expression system for the production of recombinant protein in human 293S cells," *Cytotechnology*, 15(1-3):145-155, 1994.

Gilbert, "Adaptation of cells to serum free culture for production of adenovirus vectors and recombinant proteins," *Williamsburg BioProcessing Conference*, Nov. 18-21, 1996.

Goldstein et al, "Defective lipoprotein receptors and atherosclerosis—lessons from an animal counterpart of familial hypercholesterolemia," *New Engl. J. Med.*, 309(11983):288-296, 1983.

Graham and Prevec, "Manipulation of adenovirus vectors," In: *Methods in Molecular Biology: Gene Transfer and Expression Protocol*, Murray (Ed.), Humana Press, Clifton, NJ, vol. 7: Chapter 11, pp. 109-127, 1991.

Graham and Prevec, "Methods for construction of adenovirus vectors," *Mol. Biotechnol.*, 3(3):207-220, 1995.

Graham et al., "Characteristics of a human cell line transformed by DNA from human adenovirus type 5," *J. Gen. Virol.*, 36(1):59-74, 1977.

Graham, "Growth of 293 cells in suspension culture," *J. Gen. Virol.*, 68(Pt 3):937-940, 1987.

Green et al., "A new scalable method for the purification of recombinant adenovirus vectors," *Human Gene Therapy*, 13:1921-1934, 2002.

Han et al., "Receptor-mediated gene transfer to cells of hepatic origin by galactosylated albumin-polylysine complexes," *Biol. Pharm. Bull.*, 22(8):836-840, 1999.

Hermens and Verhaagen, "Viral vectors, tools for the gene transfer in the nervous system," *Prog. Neurobiol.*, 55(4):399-432, 1998.

Hollstein et al., "p53 mutations in human cancers," *Science*, 253(5015):49-53, 1991.

Hurwitz et al., "Suicide gene therapy for treatment of retinoblastoma in a murine model," *Hum. Gene Ther.*, 10:441-448, 1999.

Huyghe et al., "Purification of a type 5 recombinant adenovirus encoding human p53 by column chromatography," *Human Gene Therapy*, 6:1403-1416, 1995.

Irie et al., "Therapeutic efficacy of an adenovirus-mediated anti-Hras ribozyme in experimental bladder cancer," *Antisense Nucleic Acid Drug Dev.*, 9(4):341-349, 1999.

Ishibashi et al, "Hypercholesterolemia in low density lipoprotein receptor knockout mice and its reversal by adenovirus-mediated gene delivery," *J. Clin. Invest.*, 92:883-893, 1993.

Ishibashi et al, "Massive xanthomatosis and atherosclerosis in cholesterol-fed low density lipoprotein receptor-negative mice," *J. Clin. Invest.*, 93:1885-1893, 1994.

Jardon and Garnier, "pH, $pCO_2$, and temperature effect on r-adenovirus production," *Biotechnol Prog.*, 19(1):202-208, 2003.

Jiang et al., "The melanoma differentiation associated gene mda-7 suppresses cancer cell growth," *Proc. Nat'l Acad. Sci.* USA, 93:9160-9165, 1996.

Jones and Shenk, "Isolation of deletion and substitution mutants of adenovirus type 5," *Cell*, 13:181-188, 1978.

Lesch, "Gene transfer to the brain: emerging therapeutic strategy in psychiatry?" *Biol. Psychiatry*, 45(3):247-253, 1999.

Marienfeld et al., "Autoreplication' of the vector genome in recombinant adenoviral vectors with different E1 region deletions and transgenes," *Gene Ther.*, 6(6):1101-1113, 1999.

McGrath et al., "Retrovirus purification: method that conserves envelope glycoprotein and maximizes infectivity," *J. Virol.*, 25(3):923-927, 1978.

Mincheff et al., "Naked DNA and adenoviral immunizations form immunotherapy of prostate cancer: a phase I/II clinical trial," *Eur. Urol.*, 38(2):208-217, 2000.

Mizrahi, "Production of human interferons: an overview," *Dev. Biol. Stand.*, 55:219-230, 1983.

Morris et al., "Cell cycle traverse in AHH-1 tk +/− human lymphoblastoid cells exposed to the chromosomal mutagen, m-Amsa," *Environ. Mol. Mutagen.*, 27(1):10-18, 1996.

Morrison et al., "Complete DNA sequence of canine adenovirus type 1," *J. Gen. Virol.*, 78(Pt 4):873-878, 1997.

Nadeau and Kamen, "Production of adenovirus vector for gene therapy," *Biotechnology Advances*, 20:475-489, 2003.

Nadeau et al., "Low-protein medium affects the 293SF central metabolism during growth and infection with adenovirus," *Biotech. Bioeng.*, 77(1):91-104, 2002.

O'Neil and Balkovic, "Virus harvesting ad affinity-based liquid chormatography," *Biotechnology*, 11(2):173-178, 1993.

Perrin, "An experimental rabies vaccine produced with a new BHK-21 suspension cell culture process: use of serum-free medium and perfusion-reactor system," *Vaccine*, 13(13):1244-1250, 1995.

Petrof, "Respiratory muscles and a target for adenovirus-mediated gene therapy," *Eur. Respir. J.*, 11(2):492-947, 1998.

Phillips et al., "Experience in the cultivation of mammalian cells on the 8000 l scale," *In: Large Scale Mammalian Cell Culture* (Feder and Tolbert, eds.), Academic Press, FL, pp. 87-95, 1985.

Reddy et al., "Nucleotide sequence and transcription map of porcine adenovirus type 3," *Virology*, 251(2):414-426, 1998.

Robbins and Ghivizzani, "Viral vectors for gene therapy," *Pharmacol Ther*, 80(1):35-47, 1998.

Robbins et al., "Viral vectors for gene therapy," *Trends Biotechnol.*, 16(1):35-40, 1998.

Smith and Lee, "Large-scale isolation and partial purification of type C RNA viruses on hydroxyapatite," *Anal Biochem.*, 86(1):252-263, 1978.

Stewart et al., "Adenovector-mediated gene delivery of interleukin-2 in metastatic breast cancer and melanoma:L results of a phase 1 clinical trial," *Gene Ther.*, 6(3):350-363, 1999.

Su et al., "Alterations in pancreatic, biliary, and breast carcinomas support MKK4 as a genetically targeted tumor suppressor gene," *Cancer Res.*, 58:2339-2242, 1998.

Tanzawa et al, "WHHL-rabbit: a low density lipoprotein receptor-deficient animal model for familial hypercholesterolemia," *FEBS Letters*, 118(1):81-84, 1980.

van Wezel, "Growth of cell-strains and primary cells on micro-carriers in homogeneous culture," *Nature*, 216:64-65, 1967.

Vanderkwaak and Alvarez, "Immune directed therapy for ovarian carcinoma," *Curr. Opin. Obstet. Gynecol.*, 11(1):29-34, 1999.

Wang et al., "High cell density perfusion culture of hybridoma cells for production of monoclonal antibodies in the celligen packed bed reactor," In: *Animal Cell Technology: Basic and Applied Aspects*, Kaminogawa et al., (eds), 5:463-469, Kluwer Academic Publishers, Netherlands, 1993.

Wang et al., "Modified CelliGen-packed bed bioreactors for hybridoma cell culture," *Cytotechnology*, 9:41-49, 1992.

Watanabe, "Serial Inbreeding of Rabbits with Hereditary Hyperlipdemia (WHHL-Rabbit): Incidence and Development of Atherosclerosis and Xanthoma," *Atherosclerosis*, 36:261-268, 1986.

Weinberg, "Tumor suppressor genes," *Science*, 254(5035):1138-1146, 1991.

Wilson, "Vehicles for gene therapy," *Nature*, 365:691-692, 1993.

Wilson, "When bad gene transfer is good," *J. Clin. Invest.*, 98(11):2435, 1996.

Xie et al., "Serum-free suspension cultivation of PER.C6 cells and recombinant adenovirus production under different pH conditions," *Biotechnol. Bioeng.*, 80:569-579, 2002.

Yotnda et al., "Efficient infection of primitive hematopoietic stem cells by modified adenovirus," *Gene Ther.*, 8:930-937, 2001.

Zheng et al., "Transcription units of E1a, E1b and pIX regions of bovine adenovirus type 3," *J. Gen. Virol.*, 80(Pt 7):1735-1742, 1999.

Notification of the First Office Action, issued in Chinese Patent Application No. 200480018587.3, dated Aug. 17, 2007.

* cited by examiner

METHODS AND COMPOSITIONS FOR THE PRODUCTION OF ADENOVIRAL VECTORS

This application is a divisional of U.S. patent application Ser. No. 10/439,278, filed on May 15, 2003, now abandoned, the entire contents of which is herein specifically incorporated by reference in its entirety.

BACKGROUND OF THE INVENTION

1. Field of the Invention

The present invention relates generally to the fields of cell culture and virus production. More particularly, it concerns improved methods for the culturing of mammalian cells, infection of those cells with adenovirus and the production and purification of infectious adenovirus particles therefrom.

2. Description of Related Art

A variety of cancer and genetic diseases currently are being addressed by gene therapy. Viruses are highly efficient at nucleic acid delivery to specific cell types, while often avoiding detection by the infected host's immune system. These features make certain viruses attractive candidates as gene-delivery vehicles for use in gene therapies (Robbins and Ghivizzani, 1998; Cristiano et al., 1998). Modified adenoviruses that are replication incompetent and therefore non-pathogenic are being used as vehicles to deliver therapeutic genes for a number of metabolic and oncologic disorders. These adenoviral vectors may be particularly suitable for disorders such as cancer that would best be treated by transient therapeutic gene expression since the DNA is not integrated into the host genome and the transgene expression is limited. Adenoviral vector may also be of significant benefit in gene replacement therapies, wherein a genetic or metabolic defect or deficiency is remedied by providing for expression of a replacement gene encoding a product that remedies the defect or deficiency.

Adenoviruses can be modified to efficiently deliver a therapeutic or reporter transgene to a variety of cell types. Recombinant adenoviruses types 2 and 5 (Ad2 and AdV5, respectively), which cause respiratory disease in humans, are among those currently being developed for gene therapy. Both Ad2 and AdV5 belong to a subclass of adenovirus that are not associated with human malignancies. Recently, the hybrid adenoviral vector AdV5/F35 has been developed and proven of great interest in gene therapies and related studies (Yotnda et al., 2001).

Recombinant adenoviruses are capable of providing extremely high levels of transgene delivery. The efficacy of this system in delivering a therapeutic transgene in vivo that complements a genetic imbalance has been demonstrated in animal models of various disorders (Watanabe, 1986; Tanzawa et al., 1980; Golasten et al., 1983; Ishibashi et al., 1993; and S. Ishibashi et al., 1994). Indeed, a recombinant replication defective adenovirus encoding a cDNA for the cystic fibrosis transmembrane regulator (CFTR) has been approved for use in at least two human CF clinical trials (Wilson, 1993). Hurwitz, et al., (1999) have shown the therapeutic effectiveness of adenoviral mediated gene therapy in a murine model of cancer (retinoblastoma).

As the clinical trials progress, the demand for clinical grade adenoviral vectors is increasing dramatically. The projected annual demand for a 300 patient clinical trial could reach approximately $6\times10^{14}$ PFU.

Traditionally, adenoviruses are produced in commercially available tissue culture flasks or "cellfactories." Adenoviral vector production has generally been performed in culture devices that supply culture surfaces for attachment of the HEK293 cells, such as T-flasks. Virus infected cells are harvested and freeze-thawed to release the viruses from the cells in the form of crude cell lysate. The produced crude cell lysate (CCL) is then purified by double CsCl gradient ultracentrifugation. The typically reported virus yield from 100 single tray cellfactories is about $6\times10^{12}$ PFU. Clearly, it becomes unfeasible to produce the required amount of virus using this traditional process. New scaleable and validatable production and purification processes have to be developed to meet the increasing demand.

The purification throughput of CsCl gradient ultracentrifugation is so limited that it cannot meet the demand for adenoviral vectors for gene therapy applications. Therefore, in order to achieve large scale adenoviral vector production, purification methods other than CsCl gradient ultracentrifugation have to be developed. Reports on the chromatographic purification of viruses are very limited, despite the wide application of chromatography for the purification of recombinant proteins. Size exclusion, ion exchange and affinity chromatography have been evaluated for the purification of retroviruses, tick-borne encephalitis virus, and plant viruses with varying degrees of success (Crooks, et al., 1990; Aboud, et al., 1982; McGrath et al., 1978; Smith and Lee, 1978; O'Neil and Balkovic, 1993). Even less research has been done on the chromatographic purification of adenobirus. This lack of research activity may be partially attributable to the existence of the effective, albeit non-scalable, CsCl gradient ultracentrifugation purification method for adenoviruses.

Recently, Huyghe et al., (1996) reported adenoviral vector purification using ion exchange chromatography in conjunction with metal chelate affinity chromatography. Virus purity similar to that from CsCl gradient ultracentrifugation was reported. Unfortunately, only 23% of virus was recovered after the double column purification process. Process factors that contribute to this low virus recovery are the freeze/thaw step utilized by the authors to lyse cells in order to release the virus from the cells and the two column purification procedure.

For most of the E1 deleted first generation adenoviral vectors, production is carried out using HEK293 cells which complement the adenoviral vector E1 deletion in trans. Because of the anchorage dependency of the HEK293 cells, adenoviral vector production has generally been performed in culture devices that supply culture surfaces for attachment of the HEK293 cells, such as T-flasks, multilayer Cellfactories™, and the large scale CellCube™ bioreactor system. Recently, the HEK293 cells have been adapted to suspension culture in a variety of serum free media allowing production of adenoviral vectors in suspension bioreactors. Complete medium exchange at the time of virus infection using centrifugation is difficult to perform on a large scale. In addition, the shear stress associated with medium recirculation required for external filtration devices is likely to have a detrimental effect on host cells in a protein-free medium.

Clearly, there is a demand for improved methods of adenoviral vector production that will recover a high yield of product to meet the ever increasing demand for such products. Improved methods for adenoviral vector production can include improved techniques to make production more efficient, or optimization of operating conditions to increase adenoviral vector production.

Studies of the operating conditions on adenoviral production and purification have been minimal. One study (Jardon and Garnier, 2003) discussed the effect of certain operating conditions, including temperature, pH, and $pCO_2$, in the context of E1 and E3 deleted Ad5 production.

SUMMARY OF THE INVENTION

The present invention is based on the discovery that when adenovirus is produced by infecting host cells grown in media, adenovirus production is maximized at infection temperatures slightly lower than 37° C. The identification of the optimal infection temperature range for adenovirus infection represents a significant improvement in the technology for producing adenoviral vectors for gene therapy.

In addition, the present invention is based on the discovery that when host cells are grown in a bioreactor, the dilution step wherein fresh media is exchanged can be combined with the adenovirus infection step. More specifically, there is no need for a separate medium exchange step. Thus, the technique for mass production of adenovirus can be more efficiently performed by combining two steps into a single step. Approximately equivalent virus productivity was attained with this method of dilution/infection relative to the standard method of centrifugation and complete medium exchange prior to infection.

Therefore, the present invention is designed to take advantage of these newly discovered improvements by providing for improved techniques related to adenovirus production and purification. Thus, the invention relates to methods related to the production and purification of adenovirus, and compositions of adenovirus that are produced and purified in accordance with these new discoveries.

Methods of the invention includes methods for producing an adenovirus, including: (1) preparing an adenovirus preparation, including the steps of growing host cells in media; and infecting the host cells with an adenovirus at a growth-permissive temperature of less than 37° C.; and (2) isolating adenovirus from the adenovirus preparation. In certain embodiments, infecting the host cells with an adenovirus is conducted at a temperature greater than 31° C. but less than 37° C. For example, infecting the host cells with an adenovirus may be conducted at a temperature within the range of 32° C. to 36° C., 33° C. to 36° C., 34° C. to 36° C., 35° C. to 36° C., or any range of temperature or increments of temperature derivable therein. In other embodiments, infecting the host cells with an adenovirus is conducted at a temperature within the range of 32° C. to less than 37° C., 33° C. to less than 37° C., 34° C. to less than 37° C., 35° C. to less than 37° C., 36° C. to less than 37° C., or any range of temperature or increments of temperature derivable therein. In other embodiments, infecting the host cells with an adenovirus may be conducted at a temperature of about 36° C., about 35° C., about 34° C., about 33° C., about 32° C., or any range of temperature or increments of temperature derivable therein.

In the disclosed embodiments of the present invention pertaining to methods for producing an adenovirus, any media for growing host cells is contemplated, as long as the media is capable of supporting the growth of host cells. In certain embodiments of the present invention, the media is DMEM+ 2% FBS. The present invention also contemplates that other substances may be added to the media to support host cell growth. One of skill in the art would be familiar with the range of substances and additives that may be used to promote cell growth. For example, in some embodiments, the glucose concentration in said media is maintained between about 0.5 and about 3.0 gm glucose/liter.

Other embodiments of the present invention pertain to methods for producing an adenovirus, including: (1) preparing an adenovirus preparation, including the steps of growing host cells in media in a bioreactor and initiating virus infection by diluting the host cells with fresh media and adenovirus; and (2) isolating adenovirus from the adenovirus preparation. Any bioreactor known to those of skill in the art that is capable of supporting host cell growth is contemplated for use in the present invention. A detailed discussion of various types of bioreactors is presented below in other parts of the specification.

The various embodiments of the present invention requiring a bioreactor contemplate that any type of media may be used in conjunction with the bioreactor, as long as the media is capable of supporting cell growth in the bioreactor. For example, the media may be serum-free media. In other embodiments, the media is protein-free media. In some embodiments, the media is CD293 media. In the embodiments of the present invention, the host cells may be grown in an anchorage-dependent culture or a non-anchorage-dependent (suspension) culture.

In the embodiments of the present invention that pertain to methods of producing an adenovirus which require a bioreactor, any bioreactor known to those of skill in the art is contemplated by the present invention. In certain embodiments, for example, the bioreactor comprises a bioreactor that uses axial rocking of a planar platform to induce wave motions inside of the bioreactor. In some embodiments, wave motions are induced inside of a sterilized polyethylene bag wherein the host cells are located. In further embodiments, the bioreactor is a disposable bioreactor. Any size of bioreactor is contemplated by the present invention. For example, the bioreactor may be a 10 L bioreactor. In addition, the bioreactor may be a commercially-available bioreactor. For example, the bioreactor may be a Wave Bioreactor® (Wave Biotech, LLC, Bedminster, N.J.).

In the embodiments of the present invention that pertain to methods of producing an adenovirus, it is contemplated that the operating conditions of the cell culture may be monitored or measured by any technique known to those of skill in the art. Examples of such conditions which may be monitored include pH of the media and dissolved oxygen tension of the media.

Some embodiments of the present invention pertaining to methods of producing an adenovirus also involve processing and treating the media by any method known to those of skill in the art. For example, in certain embodiments of the present invention, the methods for producing an adenovirus involve perfusing the media through a filter. The filter may be a filter that is internal to the bioreactor system, or the filter may be incorporated so that it is external to the bioreactor. In certain embodiments, the filter is a floating flat filter. The floating flat filter may be used to remove spent media from the bioreactor. Any method known to those of skill in the art may be used to monitor and maintain media volume. In some embodiments, culture volume is maintained by a load cell used to trigger fresh media addition.

In embodiments of the present invention, media may or may not be perfused into the culture of host cells. In some embodiments of the present invention, media is perfused beginning on day 3 of host cell growth. One of skill in the art would be familiar with the wide range of techniques and apparatus available for perfusing media into a cell culture system.

In embodiments of the present invention that pertain to methods of producing an adenovirus, the step of diluting host cells with fresh media may be combined with the adenovirus infection step. This is based on the inventors' discovery that these two steps can be efficiently combined to provide for excellent yields of adenoviral vectors. The invention contemplates use of any method of dilution known to those of skill in the art. In certain embodiments, the host cells are diluted 2-fold to 50-fold with fresh media and adenovirus. In other embodiments, the host cells are diluted 10-fold with fresh media and adenovirus.

In the embodiments of the present invention that pertain to methods of producing an adenovirus, the initiating of virus infection of the host cells may be accomplished by any method known to those of skill in the art. For example, in embodiments of the present invention that involve use of bioreactors, the virus infection may take place in a second bioreactor. For example, virus infection of host cells may be accomplished by adding 20-100 vp/host cell. In certain other embodiments, virus infection involves adding about 50 vp/host cell. Virus infection may be allowed to proceed for any duration of time. One of skill in the art would be familiar with techniques pertaining to monitoring the progress of virus infection. In certain embodiments of the present invention, virus infection is allowed to proceed for about 4 days. In certain other embodiments of the present invention, the isolating of the adenovirus from the adenovirus preparation occurs at about 4 days after viral infection is completed.

In the embodiments of the present invention that involve production of adenovirus, use of host cells is contemplated. Any cell type can be used as a host cell, as long as the cell is capable of supporting replication of adenovirus. One of skill in the art would be familiar with the wide range of host cells that can be used in the production of adenovirus from host cells. For example, in some embodiments of the present invention, the host cells complement the growth of the replication-deficient adenovirus. The replication-deficient adenovirus may be an adenovirus that lacks at least a portion of the E1-region, or it may be an adenovirus that lacks at least a portion of the E1A and/or E1B region. The host cells, for example, may be 293, HEK293, PER.C6, 911, and IT293SF cells. In certain embodiments of the present invention, the host cells are HEK293 cells.

In some embodiments of the present invention, the adenovirus is a recombinant adenovirus. For example, the recombinant adenovirus may encode a recombinant gene that is operatively linked to a promoter. Any promoter known to those of skill in the art can be used, as long as the promoter is capable of functioning as a promoter. For example, in certain embodiments the promoter is an SV40 EI, RSV LTR, β-actin, CMV-IE, adenovirus major late, polyoma F9-1, or tyrosinase promoter.

In embodiments of the present invention where the adenovirus is an adenovirus encoding a recombinant gene, any recombinant gene, particularly a therapeutic gene, is contemplated by the present invention. For example, the recombinant gene may be selected from the group consisting of antisense ras, antisense myc, antisense raf antisense erb, antisense src, antisense fms, antisense jun, antisense trk, antisense ret, antisense gsp, antisense hst, antisense bcl antisense abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus, interferon α, interferon β, interferon γ, ADP (adenoviral death protein), or p53. In some embodiments, the recombinant gene is a p53 gene. In other embodiments, the recombinant gene is a mda-7 gene.

In some embodiments of the present invention, the recombinant gene is antisense ras, antisense myc, antisense raf, antisense erb, antisense src, antisense fms, antisense jun, antisense trk, antisense ret, antisense gsp, antisense hst, antisense bcl antisense abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, Rb, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

In further embodiments of the present invention, the recombinant gene is a gene encoding an ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidase, a pullanase, a recombinase, a reverse transcriptase, a topoisomerase, a xylanase, a reporter gene, an interleukin, or a cytokine.

In other embodiments of the present invention, the recombinant gene is a gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta.-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, or human thymidine kinase. Alternatively, the recombinant gene may encode growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

Certain of the embodiments of the present invention pertain to methods of producing an adenovirus that involve isolating the adenovirus from an adenovirus preparation. Any method of isolating the adenovirus from the adenovirus preparation known to those of skill in the art is contemplated by the present invention. In certain embodiments of the present invention, the host cells are harvested following infection but prior to lysis by the adenovirus, and lysing the host cells is performed by freeze-thaw, autolysis, or detergent lysis. In certain other embodiments of the present invention, the methods of producing adenovirus involve reducing the concentration of contaminating nucleic acids in the adenovirus preparation.

In some embodiments of the invention, the adenovirus that is isolated is placed into a pharmaceutically acceptable composition. One of skill in the art would be familiar with the extensive methods and techniques employed in preparing pharmaceutically acceptable compositions. Any pharmaceutical composition into which adenovirus can be formulated is contemplated by the present invention. For example, certain embodiments of the invention pertain to pharmaceutical preparation of adenovirus for oral administration, topical administration, or intravenous administration.

Certain embodiments of the present invention involve methods of purifying an adenovirus that has been isolated from an adenovirus preparation. One of skill in the art would be familiar with the wide range of techniques available for purifying adenovirus. For example, purifying the adenovirus may involve a chromatography step. In some embodiments of the invention, the chromatography step include subjecting the adenovirus to more than one chromatographic separation whereas in other embodiments the chromatography step involves subjecting the adenovirus to only one chromatographic separation. In other embodiments, the chromatographic separation includes ion exchange chromatography.

Some embodiments of the present invention involve analysis of virus production. For example, virus production may be analyzed using HPLC. Any technique for analyzing virus production known to those of skill is contemplated by the present invention.

In some embodiments of the invention, the methods for producing an adenovirus disclosed above and elsewhere in this specification concern methods for isolating and purifying an adenovirus that involve obtaining a purified adenovirus composition having one or more of the following properties: (1) a virus titer of between $1 \times 10^9$ and about $1 \times 10^{13}$ pfu/ml; (2) a virus particle concentration between about $1 \times 10^{10}$ and about $2 \times 10^{13}$ particles/ml; (3) a particle:pfu ration between about 10 and about 60; (4) having less than 50 ng BSA per 1×10e12 viral particles; (5) between about 50 pg and 1 ng of contaminating human DNA per $1 \times 10^{12}$ viral particles; (6) a single HPLC elution peak consisting essentially of 97% to 99% of the area under the peak. In certain embodiments, the adenovirus composition prepared in accordance with the steps discussed above includes between $5 \times 10^{14}$ and $1 \times 10^{18}$ viral particles. In other embodiments, the composition is a pharmaceutically-acceptable composition.

Some embodiments of the present invention, the methods of producing an adenovirus discussed above and elsewhere in this specification involve isolating the adenovirus from the adenovirus preparation comprises the steps of: (1) subjecting the adenovirus preparation to chromatography on a first chromatographic medium, whereby adenovirus particles are retained on the first chromatographic medium; (2) eluting adenovirus particles from the first chromatographic medium to produce an eluate of adenovirus particles; (3) subjecting adenovirus particles from the eluate to chromatography on a second chromatographic medium, wherein the second chromatographic medium retains one or more contaminants from the eluate and wherein the second chromotographic medium is not solely a size exclusion medium; and (4) collecting adenovirus particles from the eluate. In certain embodiments, the first chromatographic medium is selected from the group consisting of an anion exchange medium, cation exchange medium, immobilized metal affinity medium, sulfated affinity media, immunoaffinity medium, heparin affinity medium, hydroxyapetite medium, and hydrophobin interaction medium. In other embodiments, the second chromatographic medium is selected from the group consisting of cation exchange media, anion exchange media, immobilized metal affinity media, sulfated affinity media, dye affinity media, hydroxyapetite media, immunoaffinity media, heparin affinity media, and hydrophobic interaction media.

In other embodiments of the present invention, the methods of producing an adenovirus discussed above and elsewhere in this specification involve isolating the adenovirus from the adenovirus preparation comprises the steps of: (1) subjecting the adenovirus preparation to chromatography on a first chromatographic medium, whereby contaminants from the adenovirus preparation are retained on the first chromatographic medium; (2) subjecting adenovirus particles remaining in the eluant to chromatography on a second chromatographic medium wheregy adenovirus particles from the eluant are retained on the second chromatographic medium, wherein when the second chromatographic medium is an anion exchange medium, then the first chromatographic medium is a medium other than a sulfonated polysaccharide affinity medium, and (3) eluting adenovirus particles from the second chromatographic medium. In certain embodiments, the first chromatographic medium is selected from the group consisting of an anion exchange medium, cation exchange medium, immobilized metal affinity medium, sulfated affinity media, immunoaffinity medium, heparin affinity medium, hydroxyapetite medium, and hydrophobin interaction medium. In other embodiments, the second chromatographic medium is selected from the group consisting of cation exchange media, anion exchange media, immobilized metal affinity media, sulfated affinity media, dye affinity media, hydroxyapetite media, immunoaffinity media, heparin affinity media, and hydrophobic interaction media. Any chromatographic media known to those of skill in the art is contemplated by the present invention. One of skill in the art would be familiar with the range of media available to practice the claimed invention.

It is contemplated that embodiments discussed herein with respect to one method of the invention may be implemented with respect to other methods of the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
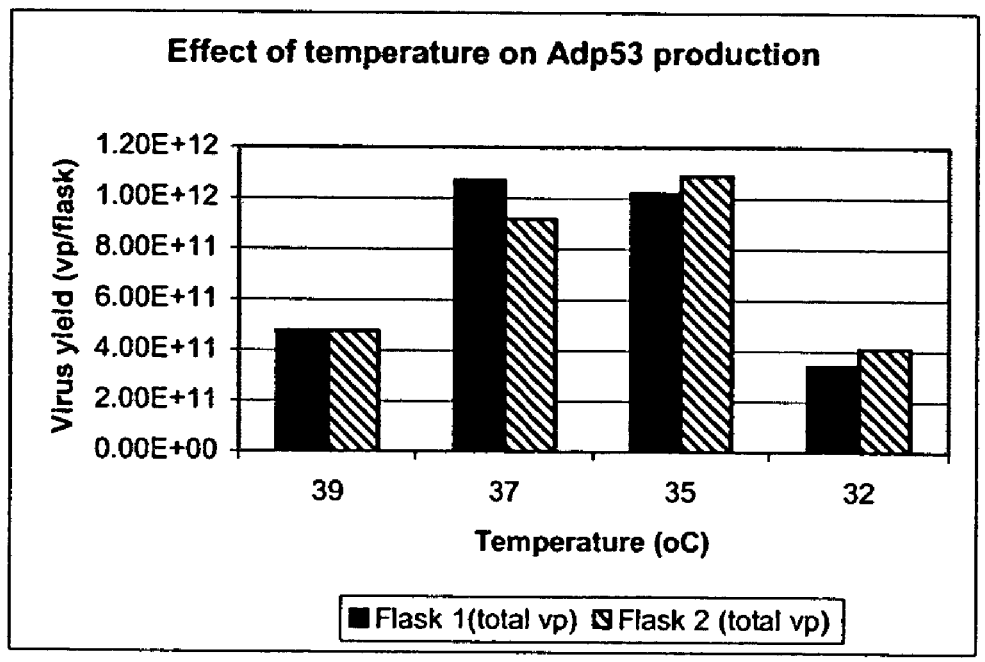
FIG. 1A show results of a study demonstrating the effect of temperature on Adp53 production (vp/flask).

It has been shown that adenoviral vectors can successfully be used in eukaryotic gene expression and vaccine development. There is mounting evidence that adenovirus can be used for gene therapy. Successful studies in administering recombinant adenovirus to different tissues have proven the effectiveness of adenoviral vectors in gene therapy. This success has led to the use of such vectors in human clinical trials. There now is an increased demand for the production of adenoviral vectors to be used in various therapies. The techniques currently available are insufficient to meet such a demand. The present invention provides methods for the production and purification of large amounts of adenovirus for use in such therapies.

The inventors have made the surprising discovery that adenovirus production is maximized at temperatures slightly lower than 37° C. The identification of the optimal infection temperature range for adenovirus infection represents a significant improvement in the technology for producing adenoviral vectors for gene therapy.

In addition, the inventors have discovered that when host cells are grown in a bioreactor, the dilution step wherein fresh media is exchanged can be combined with the adenovirus infection step without loss of virus production. More specifically, there is no need for a separate medium exchange step. Thus, the technique for mass production of adenovirus can be more efficiently performed by combining two steps into a single step.

Therefore, the present invention is designed to take advantage of these improvements in large scale culturing systems and purification for the purpose of producing and purifying adenoviral vectors. Methods for producing and purifying adenovirus using the novel findings of the inventors are set forth in detail below.

A. Adenovirus

Adenoviruses comprise linear double stranded DNA, with a genome ranging from 30 to 35 kb in size (Reddy et al., 1998; Morrison et al., 1997; Chillon et al., 1999). There are over 50 serotypes of human adenovirus, and over 80 related forms which are divided into six families based on immunological, molecular, and functional criteria (Wadell et al, 1980). Physically, adenovirus is a medium-sized icosahedral virus containing a double-stranded, linear DNA genome which, for adenovirus type 5, is 35,935 base pairs (Chroboczek et al., 1992). Adenoviruses require entry into the host cell and transport of the viral genome to the nucleus for infection of the cell and replication of the virus.

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a ψ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, function as origins of replication and are necessary for viral DNA replication. The ψ sequence is required for the packaging of the adenoviral genome.

The mechanism of infection by adenoviruses, particularly adenovirus serotypes 2 and 5, has been extensively studied. A host cell surface protein designated CAR (Coxsackie Adenoviral Receptor) has been identified as the primary binding receptor for these adenoviruses. The endogenous cellular function of CAR has not yet been elucidated. Interaction between the fiber knob and CAR is sufficient for binding of the adenovirus to the cell surface. However, subsequent interactions between the penton base and additional cell surface proteins, members of the $\alpha_v$ integrin family, are necessary for efficient viral internalization. Disassembly of the adenovirus begins during internalization; the fiber proteins remain on the cell surface bound to CAR. The remainder of the adenovirus is dissembled in a stepwise manner as the viral particle is transported through the cytoplasm to a pore complex at the nuclear membrane. The viral DNA is extruded through the nuclear membrane into the nucleus where viral DNA is replicated, viral proteins are expressed, and new viral particles are assembled. Specific steps in this mechanism of adenoviral infection may be potential targets to modulate viral infection and gene expression.

In certain embodiments of the present invention, the adenovirus used in the methods for producing an adenovirus may be a replication-deficient adenovirus. For example, the adenovirus may be a replication-deficient adenovirus lacking at least a portion of the E1 region. In certain embodiments, the adenovirus may be lacking at least a portion of the E1A and/or E1B region. In other embodiments, the adenovirus is a recombinant adenovirus (discussed further below).

B. Host Cells

Various embodiments of the present invention involve methods for producing an adenovirus. A "host cell" is defined as a cell that is capable of supporting replication of adenovirus. Any cell type for use as a host cell is contemplated by the present invention invention, as long as the cell is capable of supporting replication of adenovirus. For example, the host cells may be HEK293, PER.C6, 911, or IT293SF cells. One of skill in the art would be familiar with the wide range of host cells that are available for use in methods for producing an adenovirus.

In certain embodiments, the generation and propagation of the adenoviral vectors depend on a unique helper cell line, designated 293, which was transformed from human embryonic kidney cells by Adenovirus serotype 5 (Ad5) DNA fragments and constitutively expresses E1 proteins (Graham et al., 1977). Since the E3 region is dispensable from the Ad genome (Jones and Shenk, 1978), the current Ad vectors, with the help of 293 cells, carry foreign DNA in either the E1, the E3 or both regions (Graham and Prevec, 1991; Bett et al., 1994).

The host cells used in the various embodiments of the present invention may be derived, for example, from mammalian cells such as human embryonic kidney cells or primate cells. Other cell types might include, but are not limited to Vero cells, CHO cells or any eukaryotic cells for which tissue culture techniques are established as long as the cells are adenovirus permissive. The term "adenovirus permissive"

means that the adenovirus or adenoviral vector is able to complete the entire intracellular virus life cycle within the cellular environment.

The host cell may be derived from an existing cell line, e.g., from a 293 cell line, or developed de novo. Such host cells express the adenoviral genes necessary to complement in trans deletions in an adenoviral genome or which supports replication of an otherwise defective adenoviral vector, such as the E1, E2, E4, E5 and late functions. A particular portion of the adenovirus genome, the E1 region, has already been used to generate complementing cell lines. Whether integrated or episomal, portions of the adenovirus genome lacking a viral origin of replication, when introduced into a cell line, will not replicate even when the cell is superinfected with wild-type adenovirus. In addition, because the transcription of the major late unit is after viral DNA replication, the late functions of adenovirus cannot be expressed sufficiently from a cell line. Thus, the E2 regions, which overlap with late functions (L1-5), will be provided by helper viruses and not by the cell line. Typically, a cell line according to the present invention will express E1 and/or E4.

Recombinant host cells, which are host cells that express part of the adenoviral genome, are also contemplated for use as host cells in the present invention. As used herein, the term "recombinant" cell is intended to refer to a cell into which a gene, such as a gene from the adenovirus genome or from another cell, has been introduced. Therefore, recombinant cells are distinguishable from naturally-occurring cells which do not contain a recombinantly-introduced gene. Recombinant cells are thus cells having a gene or genes introduced through "the hand of man."

Recombinant host cells lines are capable of supporting replication of adenovirus recombinant vectors and helper viruses having defects in certain adenoviral genes, i.e., are "permissive" for growth of these viruses and vectors. The recombinant cell also is referred to as a helper cell because of the ability to complement defects in, and support replication of, replication-incompetent adenoviral vectors.

Examples of other useful mammalian cell lines that may be used with a replication competent virus or converted into complementing host cells for use with replication deficient virus are Vero and HeLa cells and cell lines of Chinese hamster ovary, W138, BHK, COS-7, HepG2, 3T3, RIN and MDCK cells.

In certain embodiments, it may be useful to employ selection systems that preclude growth of undesirable cells. This may be accomplished by virtue of permanently transforming a cell line with a selectable marker or by transducing or infecting a cell line with a viral vector that encodes a selectable marker. In either situation, culture of the transformed/ transduced cell with an appropriate drug or selective compound will result in the enhancement, in the cell population, of those cells carrying the marker.

Examples of markers include, but are not limited to, HSV thymidine kinase, hypoxanthine-guanine phosphoribosyl-transferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; and hygro, that confers resistance to hygromycin.

Serum weaning adaptation of anchorage-dependent cells into serum-free suspension cultures have been used for the production of recombinant proteins (Berg, 1993) and viral vaccines (Perrin, 1995). There have been few reports on the adaptation of 293A cells into serum-free suspension cultures until recently. Gilbert reported the adaptation of 293A cells into serum-free suspension cultures for adenovirus and recombinant protein production (Gilbert, 1996). Similar adaptation method had been used for the adaptation of A549 cells into serum-free suspension culture for adenovirus production (Morris et al., 1996). Cell-specific virus yields in the adapted suspension cells, however, are about 5-10-fold lower than those achieved in the parental attached cells.

Two methodologies have been used to adapt 293 cells into suspension cultures. Graham adapted 293A cells into suspension culture (293N3S cells) by 3 serial passages in nude mice (Graham, 1987). The suspension 293N3S cells were found to be capable of supporting E1⁻ adenoviral vectors. However, Garnier et al. (1994) observed that the 293N35 cells had a relatively long initial lag phase in suspension, a low growth rate, and a strong tendency to clump.

The second method that has been used is a gradual adaptation of 293A cells into suspension growth (Cold Spring Harbor Laboratories, 293S cells). Garnier et al. (1994) reported the use of 293S cells for production of recombinant proteins from adenoviral vectors. The authors found that 293S cells were much less clumpy in calcium-free media and a fresh medium exchange at the time of virus infection could significantly increase the protein production. It was found that glucose was the limiting factor in culture without medium exchange.

C. Cell Culture Systems

The ability to produce infectious viral vectors is increasingly important to the pharmaceutical industry, especially in the context of gene therapy. Over the last decade, advances in biotechnology have led to the production of a number of important viral vectors that have potential uses as therapies, vaccines and protein production machines. The use of viral vectors in mammalian cultures has advantages over proteins produced in bacterial or other lower life form hosts in their ability to post-translationally process complex protein structures such as disulfide-dependent folding and glycosylation.

Development of cell culture for production of virus vectors has been greatly aided by the development in molecular biology of techniques for design and construction of vector systems highly efficient in mammalian cell cultures, a battery of useful selection markers, gene amplification schemes and a more comprehensive understanding of the biochemical and cellular mechanisms involved in procuring the final biologically-active molecule from the introduced vector.

PCT publication No. WO 98/00524, U.S. Pat. No. 6,194, 191, U.S. Published Patent Application No. US-2002-0182723-A1, and U.S. Provisional Patent Application No. 60/406,591 (filed Aug. 28, 2002), which have described viral production methods, are specifically herein incorporated by reference for their description of techniques for culturing, production and purification of recombinant viral particles.

Certain embodiments of the present invention pertain to methods for producing an adenovirus that require the use of a bioreactor. As used herein, a "bioreactor" refers to any apparatus that can be used for the purpose of culturing cells. Growing cells according to the present invention in a bioreactor allows for large scale production of fully biologically-active cells capable of being infected by the adenoviral vectors of the present invention.

Bioreactors have been widely used for the production of biological products from both suspension and anchorage dependent cell cultures. The most widely used producer cells for adenoviral vector production are anchorage dependent human embryonic kidney cells (293 cells). Bioreactors to be developed for adenoviral vector production should have the characteristic of high volume-specific culture surface area in order to achieve high producer cell density and high virus yield. Microcarrier cell culture in stirred tank bioreactor provides very high volume-specific culture surface area and has been used for the production of viral vaccines (Griffiths, 1986). Furthermore, stirred tank bioreactors have industrially been proven to be scaleable. The multiplate Cellcube™ cell culture system manufactured by Corning-Costar also offers a very high volume-specific culture surface area. Cells grow on both sides of the culture plates hermetically sealed together in the shape of a compact cube. Unlike stirred tank bioreactors, the Cellcube™ culture unit is disposable. This is very desirable at the early stage production of clinical product because of the reduced capital expenditure, quality control and quality assurance costs associated with disposable systems. In consideration of the advantages offered by the different systems, both the stirred tank bioreactor and the Cellcube™ system were evaluated for the production of adenovirus.

Certain embodiments of the present invention require the use of a Wave Bioreactor®, particularly for use in methods for generating adenovirus in serum-free suspension cultures. The Wave Bioreactor® is a pre-sterilized disposable bioreactor system that can be easily retrofitted with a variety of cleanroom configurations without requiring expensive CIP and SIP process utilities. The Wave Bioreactor® can be a Wave Biotech® model 20/50EH. The bioreactor can hold any volume of media, but in a certain embodiment the bioreactor is a 10 L (5L working volume) bioreactor. In certain embodiments, the bioreactor can be adjusted to rock at a particular speed and angle. In certain other embodiments, the bioreactor may include a device for monitoring dissolved oxygen tension, such as a disposable dissolved oxygen tension (DOT) probe. The bioreactor may also include a device for monitoring temperature in the media. Other embodiments include a device for measuring and adjusting culture pH, such as a gas mixer which can adjust $CO_2$ gas percentage delivered to the media. The bioreactor may or may not be a disposable bioreactor.

As used herein, "media" and "medium" refers to any substance which can facilitate growth of cells. One of skill in the art would be familiar with the wide range of types of media available which can be used in cell culture systems. In certain embodiments of the present invention, the host cells are grown in media that is serum-free media. In other embodiments of the present invention, the host cells are grown in media that is protein-free media. One example of a protein-free media is CD293. Another example of media that can support host cell growth in a particular embodiment of the invention is DMEM+2% FBS. On of skill in the art would understand that various components and agents can be added to the media to facilitate and control cell growth. For example, the glucose concentration of the media can be maintained at a certain level. In one embodiment of the present methods for producing adenovirus, the glucose concentration is maintained between about 0.5 and about 3.0 gm glucose/liter.

1. Anchorage-Dependent Versus Non-Anchorage-Dependent Cultures

In some embodiments of the present invention, the methods for producing an adenovirus require growing host cells in anchorage-dependent cultures, whereas other embodiments pertain to methods for producing an adenovirus in non-anchorage-dependent cultures. Animal and human cells can be propagated in vitro in two modes: as non-anchorage dependent cells growing freely in suspension throughout the bulk of the culture; or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. Bioreactors are frequently employed in suspension culture systems. In the context of the present invention, however, bioreactors may also be used in anchorage-dependent cultures. Large scale suspension culture can provide advantages in viral vector production. For example, the processes are relatively simple to operate and straightforward to scale up. As discussed above, homogeneous conditions can be provided in the bioreactor which allows for precise monitoring and control of culture conditions such as dissolved oxygen, and pH.

2. Bioreactors and Processes for Suspension

The bioreactors utilized in the context of selected embodiments of the present invention may be stirred tank bioreactors. Large scale suspension culture of mammalian cultures in stirred tanks have been described. The instrumentation and controls for bioreactors adapted, along with the design of the fermentors, from related microbial applications. However, acknowledging the increased demand for contamination control in the slower growing mammalian cultures, improved aseptic designs were quickly implemented, improving dependability of these reactors. Instrumentation and controls are basically the same as found in other fermentors and include agitation, temperature, dissolved oxygen, and pH controls. More advanced probes and autoanalyzers for on-line and off-line measurements of turbidity (a function of particles present), capacitance (a function of viable cells present), glucose/actate, carbonate/bicarbonate and carbon dioxide are available. In one embodiment of the present invention, the autoanalyzer is a YSI-2700 SELECT™ analyzer.

Two suspension culture bioreactor designs are widely used in the industry due to their simplicity and robustness of operation—the stirred bioreactor and the airlift bioreactor. The stirred bioreactor design has successfully been used on a scale of 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

In certain embodiments of the present invention, the bioreactor includes axial rocking of a planar platform to induce wave motions inside of the bioreactor. In other embodiments, the wave motions are induced inside of a sterilized bag made of layers of polyethylene vinyl acetate and ethyl vinyl alcohol.

The airlift bioreactor, also initially described for microbial fermentation and later adapted for mammalian culture, relies on a gas stream to both mix and oxygenate the culture. The gas stream enters a riser section of the bioreactor and drives circulation. Gas disengages at the culture surface, causing denser liquid free of gas bubbles to travel downward in the downcomer section of the bioreactor. The main advantage of this design is the simplicity and lack of need for mechanical mixing. Typically, the height-to-diameter ratio is 10:1. The airlift reactor scales up relatively easily, has good mass transfer of gasses and generates relatively low shear forces.

Most large-scale suspension cultures are operated as batch or fed-batch processes because they are the most straightforward to operate and scale up. However, continuous processes based on chemostat or perfusion principles are available.

A batch process is a closed system in which a typical growth profile is seen. A lag phase is followed by exponential, stationary and decline phases. In such a system, the environment is continuously changing as nutrients are depleted and metabolites accumulate. This makes analysis of factors influencing cell growth and productivity, and hence optimization of the process, a complex task. Productivity of a batch process may be increased by controlled feeding of key nutrients to prolong the growth cycle. Such a fed-batch process is still a closed system because cells, products and waste products are not removed.

In what is still a closed system, perfusion of fresh medium through the culture can be achieved by retaining the cells with a variety of devices (e.g. fine mesh spin filter, hollow fiber or flat plate membrane filters, settling tubes). A true open system and the simplest perfusion process is the chemostat in which there is an inflow of medium and an outflow of cells and products. Culture medium is fed to the reactor at a predetermined and constant rate which maintains the dilution rate of the culture at a value less than the maximum specific growth rate of the cells (to prevent washout of the cell mass from the reactor). Culture fluid containing cells and cell products and byproducts is removed at the same rate.

In certain embodiments of the present methods for producing adenovirus, the bioreactor system is set up to include a system to allow for media exchange. For example, filters may be incorporated into the bioreactor system to allow for separation of cells from spent media to facilitate media exchange. In some embodiments of the present methods for producing adenovirus, media exchange and perfusion is conducted beginning on a certain day of cell growth. For example, media exchange and perfusion can begin on day 3 of cell growth. The filter may be external to the bioreactor, or internal to the bioreactor.

In one embodiment of the present invention, the filter is a floating flat filter that is internal to the bioreactor. The filter provides for separation between the cells and spent medium. In certain embodiments, the spent culture media is withdrawn through the floating filer. Recirculation of the media may or may not be required in the various embodiments of the present invention. In one embodiment, wave action is used to minimize clogging of the filter during media perfusion. The culture volume may be maintained by a load cell used to trigger fresh medium addition. One of skill in the art would be familiar with the various types of filters that can be used for perfusion of media, and the various methods that can be employed for attaching the filter to the bioreactor and incorporating it into the cell growth process.

3. Non-Perfused Attachment Systems

Traditionally, anchorage-dependent cell cultures are propagated on the bottom of small glass or plastic vessels. The restricted surface-to-volume ratio offered by classical and traditional techniques, suitable for the laboratory scale, has created a bottleneck in the production of cells and cell products on a large scale. In an attempt to provide systems that offer large accessible surfaces for cell growth in small culture volume, a number of techniques have been proposed: the roller bottle system, the stack plates propagator, the spiral film bottles, the hollow fiber system, the packed bed, the plate exchanger system, and the membrane tubing reel. Since these systems are non-homogeneous in their nature, and are sometimes based on multiple processes, they suffer from the following shortcomings—limited potential for scale-up, difficulties in taking cell samples, limited potential for measuring and controlling key process parameters and difficulty in maintaining homogeneous environmental conditions throughout the culture.

Despite these drawbacks, a commonly used process for large scale anchorage-dependent cell production is the roller bottle. Being little more than a large, differently shaped T-flask, simplicity of the system makes it very dependable and, hence, attractive. Fully automated robots are available that can handle thousands of roller bottles per day, thus eliminating the risk of contamination and inconsistency associated with the otherwise required intense human handling. With frequent media changes, roller bottle cultures can achieve cell densities of close to $0.5 \times 10^6$ cells/cm$^2$ (corresponding to approximately $10^9$ cells/bottle or almost $10^7$ cells/ml of culture media).

4. Cultures on Microcarriers

In an effort to overcome the shortcomings of the traditional anchorage-dependent culture processes, van Wezel (1967) developed the concept of the microcarrier culturing systems. In this system, cells are propagated on the surface of small solid particles suspended in the growth medium by slow agitation. Cells attach to the microcarriers and grow gradually to confluency on the microcarrier surface. In fact, this large scale culture system upgrades the attachment dependent culture from a single disc process to a unit process in which both monolayer and suspension culture have been brought together. Thus, combining the necessary surface for a cell to grow with the advantages of the homogeneous suspension culture increases production.

The advantages of microcarrier cultures over most other anchorage-dependent, large-scale cultivation methods are several fold. First, microcarrier cultures offer a high surface-to-volume ratio (variable by changing the carrier concentration) which leads to high cell density yields and a potential for obtaining highly concentrated cell products. Cell yields are up to $1-2 \times 10^7$ cells/ml when cultures are propagated in a perfused reactor mode. Second, cells can be propagated in one unit process vessels instead of using many small low-productivity vessels (i.e., flasks or dishes). This results in far better nutrient utilization and a considerable saving of culture medium. Moreover, propagation in a single reactor leads to reduction in need for facility space and in the number of handling steps required per cell, thus reducing labor cost and risk of contamination. Third, the well-mixed and homogeneous microcarrier suspension culture makes it possible to monitor and control environmental conditions (e.g., pH, pO$_2$, and concentration of medium components), thus leading to more reproducible cell propagation and product recovery. Fourth, it is possible to take a representative sample for microscopic observation, chemical testing, or enumeration. Fifth, since microcarriers settle out of suspension quickly, use of a fed-batch process or harvesting of cells can be done relatively easily. Sixth, the mode of the anchorage-dependent culture propagation on the microcarriers makes it possible to use this system for other cellular manipulations, such as cell transfer without the use of proteolytic enzymes, cocultivation of cells, transplantation into animals, and perfusion of the culture using decanters, columns, fluidized beds, or hollow fibers for microcarrier retainment. Seventh, microcarrier cultures are relatively easily scaled up using conventional equipment used for cultivation of microbial and animal cells in suspension.

5. Microencapsulation of Mammalian Cells

One method which has shown to be particularly useful for culturing mammalian cells is microencapsulation. The mammalian cells are retained inside a semipermeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. Lim (1982, U.S. Pat. No. 4,352,883, incorporated herein by reference,) describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquefied by treating the droplet in a chelating agent to remove the calcium ions. Other methods use cells in a calcium solution to be dropped into a alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150-1500 µm in diameter, are easily retained in a perfused reactor using a fine-meshed screen. The ratio of capsule volume to total media volume can be maintained from as dense as 1:2 to 1:10. With intracapsular cell densities of up to $10^8$, the effective cell density in the culture is $1\text{-}5 \times 10^7$.

The advantages of microencapsulation over other processes include the protection from the deleterious effects of shear stresses which occur from sparging and agitation, the ability to easily retain beads for the purpose of using perfused systems, scale up is relatively straightforward and the ability to use the beads for implantation.

Some embodiments of the current invention include cells which are anchorage-dependent in nature. 293 cells, for example, are anchorage-dependent, and when grown in suspension, the cells will attach to each other and grow in clumps, eventually suffocating cells in the inner core of each clump as they reach a size that leaves the core cells unsustainable by the culture conditions. Therefore, an efficient means of large-scale culture of anchorage-dependent cells is needed in order to effectively employ these cells to generate large quantities of adenovirus.

6. Perfused Attachment Systems

Certain embodiments of the present invention involve methods for producing an adenovirus that involve use of perfused attachment systems. Perfusion refers to continuous flow at a steady rate, through or over a population of cells (of a physiological nutrient solution). It implies the retention of the cells within the culture unit as opposed to continuous-flow culture which washes the cells out with the withdrawn media (e.g., chemostat). The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential.

The current use of perfused culture is in response to the challenge of growing cells at high densities (i.e., $0.1\text{-}5 \times 10^8$ cells/ml). In order to increase densities beyond $2\text{-}4 \times 10^6$ cells/ml, the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

The development of a perfused packed-bed reactor using a bed matrix of a non-woven fabric has provided a means for maintaining a perfusion culture at densities exceeding $10^8$ cells/ml of the bed volume (CelliGen™, New Brunswick Scientific, Edison, N.J.; Wang et al., 1992; Wang et al., 1993; Wang et al., 1994). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 µm to 100 µm, providing for a high internal volume with pore volumes corresponding to 1 to 20 times the volumes of individual cells.

In comparison to other culturing systems, this approach offers several significant advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and can be produced in low-protein medium which facilitates subsequent purification steps. Also, the unique design of this reactor system offers an easier way to scale up the reactor. Currently, sizes up to 30 liter are available. One hundred liter and 300 liter versions are in development and theoretical calculations support up to a 1000 liter reactor. This technology is explained in detail in WO 94/17178 (Aug. 4, 1994, Freedman et al.), which is hereby incorporated by reference in its entirety.

The Cellcube™ (Corning-Costar) module provides a large styrenic surface area for the immobilization and growth of substrate attached cells. It is an integrally encapsulated sterile single-use device that has a series of parallel culture plate joined to create thin sealed laminar flow spaces between adjacent plates.

The Cellcube™ module has inlet and outlet ports that are diagonally opposite each other and help regulate the flow of media. During the first few days of growth the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrients composition at a variety of different perfusion rates to determine the most economical and productive operating parameters.

Cells within the system reach a higher density of solution (cells/ml) than in traditional culture systems. Many typically used basal media are designed to support $1\text{-}2 \times 10^6$ cells/ml/day. A typical Cellcube™, run with an 85,000 cm² surface, contains approximately 6 L media within the module. The cell density often exceeds $10^7$ cells/mL in the culture vessel. At confluence, 2-4 reactor volumes of media are required per day.

The timing and parameters of the production phase of cultures depends on the type and use of a particular cell line. Many cultures require a different media for production than is required for the growth phase of the culture. The transition from one phase to the other will likely require multiple washing steps in traditional cultures. However, the Cellcube™ system employs a perfusion system. On of the benefits of such a system is the ability to provide a gentle transition between various operating phases. The perfusion system negates the need for traditional wash steps that seek to remove serum components in a growth medium.

7. Serum-Free Suspension Culture

In particular embodiments, adenovirus is produced from anchorage-dependent culture of host cells (e.g., HEK293 cells). Scale-up of adenoviral vector production is constrained by the anchorage-dependency of 293A cells. To facilitate scale-up and meet future demand for adenoviral vectors, significant efforts have been devoted to the development of alternative production processes that are amenable to scale-up. Methods include growing HEK293 cells in bioreactors and adaptation of host cells into suspension cultures.

In certain embodiments of the present invention, the media used in the methods for producing an adenovirus is a serum-free media. In other embodiments of the present invention, the media is a protein-free media. One of skill in the art would understand that any media is contemplated as long as it allows for cell growth. As previously discussed, certain embodiments of the present invention involve use of bioreactors. The bioreactors may be adapted for serum-free suspension culture of cells. Filtration of media with media exchange may or may not be included in the system.

D. Viral Infection

The present invention pertains to methods of producing an adenovirus that include infecting the host cells with an adenovirus. Typically, the virus will simply be exposed to the appropriate host cell under physiologic conditions, permitting uptake of the virus. One of skill in the art would be familiar with the wide range of techniques available for initiating virus infection.

In certain embodiments of the present invention, the temperature at which infection of the host cells is performed is 37° C. However, in other embodiments, the infection temperature is at temperature that is less than 37° C. This is based on the inventors' discovery that infection temperatures less than 37° C. provide for optimal production of adenovirus. Thus, for example, the temperature may be 32.1° C., 32.2° C., 32.3° C., 32.4° C., 32.5° C., 32.6° C., 32.7° C., 32.8° C., 32.9° C., 33.0° C., 33.1° C., 33.2° C., 33.3° C., 33.4° C., 33.5° C., 33.6° C., 33.7° C., 33.8° C., 33.9° C., 34.0° C., 34.1° C., 34.2° C., 34.3° C., 34.4° C., 34.5° C., 34.6° C., 34.7° C., 34.8° C., 34.9° C., 35.0° C., 35.1° C., 35.2° C., 35.3° C., 35.4° C., 35.5° C., 35.6° C., 35.7° C., 35.8° C., 35.9° C., 36.0° C., 36.1° C., 36.2° C., 36.3° C., 36.4° C., 36.5° C., 36.6° C., 36.7° C., 36.8° C., and 36.9° C. and any range of temperature or increments of temperature derivable therein. Any method known to those of skill in the art may be used to measure the temperature of the cell culture media. One of skill in the art would be familiar with the wide range of methods available for measuring the temperature of culture media.

For example, one convenient way to measure temperature would be to use a real time digital device to measure the temperature inside an incubator. Prior to the procedure, the digital device can be calibrated using traceable temperature calibration equipment to verify accuracy of the digital device.

In certain embodiments of the present invention, the methods for producing an adenovirus may involve initiating virus infection by diluting the host cells with fresh media and adenovirus. This avoids the need for a separate medium exchange step prior to infection. The invention contemplates that any amount of dilution of the host cells is contemplated by the present invention. In a certain embodiment, the host cells are diluted 10-fold with fresh media. The invention also contemplates any amount of virus added to initiate infection. However, in a certain embodiment of the present invention, virus infection will be initiated by adding 50 vp/host cell.

The embodiments of the present invention contemplate that virus infection can be allowed to proceed for any length of time. However, in a certain embodiment, virus infection is allowed to proceed for 4 days. In another embodiment of the present invention, host cell growth is allowed to occur in one bioreactor, and infection of host cells is conducted in a second bioreactor.

The term "adenovirus preparation" will be used herein to describe the reaction mixture following initiation of infection with adenovirus. The adenovirus preparation may include host cells that have undergone lysis, cell fragments, adenovirus, media, and any other components present in the reaction mixture during infection. The adenovirus preparation may include intact host cells, depending on how long infection was allowed to proceed. Some or all of the host cells may have undergone cell lysis, with release of viral particles into the surrounding media. The present invention contemplates that in the embodiments of the methods for producing an adenovirus, adenovirus isolation will occur at any time and by any means known to those of skill in the art following infection. For example, in one embodiment of the present invention, isolating the adenovirus from the adenovirus preparation occurs 4 days after viral infection is completed.

E. Engineering of Viral Vectors

1. Viral Vectors

In particular embodiments, a recombinant adenovirus is contemplated for the delivery of expression constructs. "Recombinant adenovirus," "adenovirus vector" or "adenoviral expression vector" is meant to include those constructs containing adenovirus sequences sufficient to (a) support packaging of the construct and (b) to ultimately express a tissue or cell-specific construct that has been cloned therein. The recombinant adenovirus may encode a recombinant gene. Thus, a recombinant adenovirus may include any of the engineered vectors that comprise adenoviral sequences.

An adenovirus expression vector according to the present invention comprises a genetically engineered form of the adenovirus. The nature of the adenovirus vector is not believed to be crucial to the successful practice of the invention. The adenovirus may be of any of the known serotypes and/or subgroups A-F. Adenovirus type 5 of subgroup C is the preferred starting material in order to obtain one adenovirus vector for use in the present invention. This is because adenovirus type 5 is a human adenovirus about which a great deal of biochemical and genetic information is known, and it has historically been used for most constructions employing adenovirus as a vector.

Advantages of adenoviral gene transfer include the ability to infect a wide variety of cell types, including non-dividing cells, a mid-sized genome, ease of manipulation, high infectivity and they can be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Adenovirus growth and manipulation is known to those of skill in the art, and exhibits broad host range in vitro and in vivo (U.S. Pat. Nos. 5,670,488; 5,932,210; 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells.

Although adenovirus based vectors offer several unique advantages over other vector systems, they often are limited by vector immunogenicity, size constraints for insertion of recombinant genes, low levels of replication, and low levels of transgene expression. A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient.

Certain embodiments of the present invention pertain to methods of producing an adenovirus that involve replication-deficient adenovirus. Armentano et al., describe the preparation of a replication-deficient adenovirus vector, claimed to eliminate the potential for the inadvertent generation of a replication-competent adenovirus (U.S. Pat. No. 5,824,544). The replication-deficient adenovirus method comprises a deleted E1 region and a relocated protein IX gene, wherein the vector expresses a heterologous, mammalian gene.

A common approach for generating adenoviruses for use as a gene transfer vector is the deletion of the E1 gene (E1⁻), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1⁻, replication-deficient virus is then proliferated in a "helper" cell line that provides the E1 polypeptides in trans (e.g., the human embryonic kidney cell line 293). Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. Nos. 5,670,488; 5,932,210).

2. Viral Vectors Encoding Therapeutic Genes

In certain embodiments, the invention may include methods of producing an adenovirus where the adenovirus is a recombinant adenovirus encoding a recombinant gene. The recombinant gene may be operatively linked to a promoter. In certain other embodiments, the recombinant gene is a therapeutic gene. The invention contemplates use of any gene that has therapeutic or potential therapeutic value in the treatment of a disease or genetic disorder. One of skill in the art would be familiar with the wide range of such genes that have been identified.

Gene therapy generally involves the introduction into cells of therapeutic genes, also known as transgenes, whose expression results in amelioration or treatment of disease or genetic disorders. The therapeutic genes involved may be those that encode proteins, structural or enzymatic RNAs, inhibitory products such as antisense RNA or DNA, or any other gene product. Expression is the generation of such a gene product or the resultant effects of the generation of such a gene product. Thus, enhanced expression includes the greater production of any therapeutic gene or the augmentation of that product's role in determining the condition of the cell, tissue, organ or organism. The delivery of therapeutic genes by adenoviral vectors involves what may be termed transduction of cells. As used here, transduction is defined as the introduction into a cell a therapeutic gene, transgene, or transgene construct by an adenoviral or related vector.

Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Hermens and Verhaagen, 1998), coronary diseases (Feldman et al., 1996), muscular diseases (Petrof, 1998), and various cancers such as colorectal (Dorai et al., 1999), bladder (Irie et al., 1999), prostate (Mincheff et al., 2000), head and neck (Blackwell et al., 1999), breast (Stewart et al., 1999), lung (Batra et al., 1999) and ovarian (Vanderkwaak et al., 1999).

The particular therapeutic gene encoded by the adenoviral vector is not limiting and includes those useful for various therapeutic and research purposes, as well as reporter genes and reporter gene systems and contructs useful in tracking the expression of transgenes and the effectiveness of adenoviral and adenoviral vector transduction. Thus, by way of example, the following are classes of possible genes whose expression may be enhanced by using the compositions and methods of the present invention: developmental genes (e.g. adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), oncogenes (e.g. ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES), tumor suppresser genes (e.g. APC, BRCA1, BRCA2, MADH4, MCC, NF1, NF2, RB1, TP53 and WT1), enzymes (e.g. ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, hyaluron synthases, galactosidases, glucanases, glucose oxidases, GTPases, helicases, hemicellulases, hyaluronidases, integrases, invertases, isomersases, kinases, lactases, lipases, lipoxygenases, lyases, lysozymes, pectinesterases, peroxidases, phosphatases, phospholipases, phophorylases, polygalacturonases, proteinases and peptideases, pullanases, recombinases, reverse transcriptases, topoisomerases, xylanases), reporter genes (e.g. Green fluorescent protein and its many color variants, luciferase, CAT reporter systems, Beta-galactosidase, etc.), blood derivatives, hormones, lymphokines (including interleukins), interferons, TNF, growth factors, neurotransmitters or their precursors or synthetic enzymes, trophic factors (such as BDNF, CNTF, NGF, IGF, GMF, aFGF, bFGF, NT3, NT5, and the like), apolipoproteins (such as ApoAI, ApoAIV, ApoE, and the like), dystrophin or a minidystrophic, tumor suppressor genes (such as p53, Rb, Rap1A, DCC, k-rev, and the like), genes coding for factors involved in coagulation (such as factors VII, VI, IX, and the like), suicide genes (such as thymidine kinase), cytosine deaminase, or all or part of a natural or artificial immunoglobulin (Fab, ScFv, and the like). Other examples of therapeutic genes include fus, interferon α, interferon β, interferon γ, ADP (adenoviral death protein).

The therapeutic gene can also be an antisense gene or sequence whose expression in the target cell enables the expression of cellular genes or the transcription of cellular mRNA to be controlled, or instance ribozymes. Such sequence can, for example, be transcribed in the target cell into RNAs complementary to cellular mRNAs. The therapeutic gene can also be a gene coding for an antigenic peptide capable of generating an immune response in man. In this particular embodiment, the invention hence makes it possible to produce vaccines enabling humans to be immunized, in particular against microorganisms and viruses.

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

p53 currently is recognized as a tumor suppressor gene. High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

The p53 gene encodes a 393-amino-acid phophoprotein that can form complexes with host proteins such as large-T antigen and E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are know to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Other tumor suppressors that may be employed according to the present invention include BRCA1, BRCA2, zac1, p73, MMAC-1, ATM, HIC-1, DPC-4, FHIT, NF2, APC, DCC, PTEN, ING1, NOEY1, NOEY2, PML, OVCA1, MADR2, WT1, 53BP2, and IRF-1. Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fins, trk, ret, gsp, hst, abl, E1A, p300, genes involved in angiogenesis (e.g., VEGF, FGF, thrombospondin, BAI-1, GDAIF, or their receptors) and MCC.

In certain embodiments the adenovirus comprises an exogenous gene construct that is an mda-7 gene. MDA-7 is another putative tumor suppressor that has been shown to suppress the growth of cancer cells that are p53-wild-type, p53-null and p53-mutant. Also, the observed upregulation of the apoptosis-related Bax gene in p53 null cells indicates that MDA-7 is capable of using p53-independent mechanisms to induce the destruction of cancer cells.

Studies have shown that elevated expression of MDA-7 suppressed cancer cell growth in vitro and selectively induced apoptosis in human breast cancer cells as well as inhibiting tumor growth in nude mice (Jiang et al., 1996 and Su et al., 1998). Jiang et al. (1996) report findings that MDA-7 is a potent growth suppressing gene in cancer cells of diverse origins including breast, central nervous system, cervix, colon, prostate, and connective tissue. A colony inhibition assay was used to demonstrate that elevated expression of MDA-7 enhanced growth inhibition in human cervical carcinoma (HeLa), human breast carcinoma (MCF-7 and T47D), colon carcinoma (LS174T and SW480), nasopharyngeal carcinoma (HONE-1), prostate carcinoma (DU-145), melanoma (HO-1 and C8161), glioblastome multiforme (GBM-18 and T98G), and osteosarcoma (Saos-2). MDA-7 overexpression in normal cells (HMECs, HBL-100, and CREF-Trans6) showed limited growth inhibition indicating that MDA-7 transgene effects are not manifest in normal cells. Taken together, the data indicates that growth inhibition by elevated expression of MDA-7 is more effective in vitro in cancer cells than in normal cells. Su et al. (1998) reported investigations into the mechanism by which MDA-7 suppressed cancer cell growth. The studies reported that ectopic expression of MDA-7 in breast cancer cell lines MCF-7 and T47D induced apoptosis as detected by cell cycle analysis and TUNEL assay without an effect on the normal HBL-100 cells. Western blot analysis of cell lysates from cells infected with adenovirus MDA-7 ("Ad-MDA-7") showed an upregulation of the apoptosis stimulating protein BAX. Ad-MDA-7 infection elevated levels of BAX protein only in MCF-7 and T47D cells and not normal HBL-100 or HMEC cells. These data lead the investigators to evaluate the effect of ex vivo Ad-MDA-7 transduction on xenograft tumor formation of MCF-7 tumor cells. Ex vivo transduction resulted in the inhibition of tumor formation and progression in the tumor xenograft model. These characteristics indicate that MDA-7 has broad therapeutic, prognostic and diagnostic potential as an inducer of PKR and, consequently, an enhancer of an induced immune response.

Various enzyme genes are also considered therapeutic genes. Particularly appropriate genes for expression include those genes that are thought to be expressed at less than normal level in the target cells of the subject mammal. Examples of particularly useful gene products include carbamoyl synthetase I, ornithine transcarbamylase, arginosuccinate synthetase, arginosuccinate lyase, and arginase. Other desirable gene products include fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione .beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, .beta.-glucosidase, pyruvate carboxylase, hepatic phosphorylase, phosphorylase kinase, glycine decarboxylase (also referred to as P-protein), H-protein, T-protein, Menkes disease copper-transporting ATPase, and Wilson's disease copper-transporting ATPase. Other examples of gene products include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase. Hormones are another group of genes that may be used in the vectors described herein. Included are growth hormone, prolactin, placental lactogen, luteinizing hormone, follicle-stimulating hormone, chorionic gonadotropin, thyroid-stimulating hormone, leptin, adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, somatostatin, calcitonin, calcitonin gene related peptide (CGRP), β-calcitonin gene related peptide, hypercalcemia of malignancy factor (1-40), parathyroid hormone-related protein (107-139) (PTH-rP), parathyroid hormone-related protein (107-111) (PTH-rP), glucagon-like peptide (GLP-1), pancreastatin, pancreatic peptide, peptide YY, PHM, secretin, vasoactive intestinal peptide (VIP), oxytocin, vasopressin (AVP), vasotocin, enkephalinamide, metorphinamide, alpha melanocyte stimulating hormone (alpha-MSH), atrial natriuretic factor (5-28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH). Other classes of genes that are contemplated to be inserted into the vectors of the present invention include interleukins and cytokines. Interleukin 1 (IL-1), IL-2, IL-3, IL4, IL-5, IL-6, IL-7, IL-8, IL-9, IL-10, IL-11 IL-12, GM-CSF and G-CSF.

Examples of diseases for which the present viral vector would be useful include, but are not limited to, adenosine deaminase deficiency, human blood clotting factor IX deficiency in hemophilia B, and cystic fibrosis, which would involve the replacement of the cystic fibrosis conductance regulator gene. The vectors embodied in the present invention could also be used for treatment of hyperproliferative disorders such as rheumatoid arthritis or restenosis by transfer of genes encoding angiogenesis inhibitors or cell cycle inhibitors. Transfer of prodrug activators such as the HSV-TK gene can be also be used in the treatment of hyperploiferative disorders, including cancer.

3. Antisense Constructs

Oncogenes such as ras, myc, neu, raf erb, src, fins, jun, trk, ret, gsp, hst, bcl and abl also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementarity rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" refers to an RNA-based enzyme capable of targeting and cleaving particular base sequences in oncogene DNA and RNA. Ribozymes can either be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

4. Antigens for Vaccines

Other therapeutics genes might include genes encoding antigens such as viral antigens, bacterial antigens, fungal antigens or parasitic antigens. Viruses include picornavirus, coronavirus, togavirus, flavirvirus, rhabdovirus, paramyxovirus, orthomyxovirus, bunyavirus, arenvirus, reovirus, retrovirus, papovavirus, parvovirus, herpesvirus, poxvirus, hepadnavirus, and spongiform virus. Preferred viral targets include influenza, herpes simplex virus 1 and 2, measles, small pox, polio or HIV. Pathogens include trypanosomes, tapeworms, roundworms, helminths. Also, tumor markers, such as fetal antigen or prostate specific antigen, may be targeted in this manner. Preferred examples include HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. Preferably, vaccination of an individual would only be required infrequently, such as yearly or biennially, and provide long term immunologic protection against the infectious agent.

5. Control Regions

In order for the viral vector to effect expression of a transcript encoding a therapeutic gene, the polynucleotide encoding the therapeutic gene will be under the transcriptional control of a promoter and a polyadenylation signal. Therefore, certain embodiments of the present invention involve methods for producing an adenovirus wherein the adenovirus comprises an adenoviral vector encoding an exogenous gene construct that is operatively linked to a promoter. A "promoter" refers to a DNA sequence recognized by the synthetic machinery of the host cell, or introduced synthetic machinery, that is required to initiate the specific transcription of a gene. A polyadenylation signal refers to a DNA sequence recognized by the synthetic machinery of the host cell, or introduced synthetic machinery, that is required to direct the addition of a series of nucleotides on the end of the mRNA transcript for proper processing and trafficking of the transcript out of the nucleus into the cytoplasm for translation. The phrases "operatively linked," "under control," and "under transcriptional control" mean that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a therapeutic gene is not believed to be critical, so long as it is capable of expressing the polynucleotide in the targeted cell. The promoter may be a tissue-specific promoter or an inducible promoter. Examples of promoters that may be employed include SV40 EI, RSV LTR, β-actin, CMV-IE, adenovirus major late, polyoma F9-1, α-fetal protein promoter, egr-1, or tyrosinase promoter. One of skill in the art would be familiar with the range of options available for promoters that can be used to control the expression of a therapeutic gene. Thus, where a human cell is targeted, it is preferable to position the polynucleotide coding region adjacent to and under the control of a promoter that is capable of being expressed in a human cell. Generally speaking, such a promoter might include either a human or viral promoter. A list of promoters is provided in the Table 1.

TABLE 1

| PROMOTER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

The promoter may be a constitutive promoter, an inducible promoter, or a tissue-specific promoter. An inducible promoter is a promoter which is inactive or exhibits low activity except in the presence of an inducer substance. Some examples of promoters that may be included as a part of the present invention include, but are not limited to, MT II, MMTV, Collagenase, Stromelysin, SV40, Murine MX gene, α-2-Macroglobulin, MHC class I gene h-2kb, HSP70, Proliferin, Tumor Necrosis Factor, or Thyroid Stimulating Hormone α gene. The associated inducers are shown in Table 2. It is understood that any inducible promoter may be used in the practice of the present invention and that all such promoters would fall within the spirit and scope of the claimed invention. A promoter that is "endogenous" or "constitutive" is a promoter that is one naturally associated with a gene or sequence, as may be obtained by isolating the 5' non-coding sequences located upstream of the coding segment and/or exon.

TABLE 2

| Element | Inducer |
|---|---|
| MT II | Phorbol Ester (TPA) |
|  | Heavy metals |

TABLE 2-continued

| Element | Inducer |
|---|---|
| MMTV (mouse mammary tumor virus) | Glucocorticoids |
| β-Interferon | poly(rI)X poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2 kB | Interferon |
| HSP70 | E1a, SV40 Large T Antigen |
| Proliferin | Phorbol Ester-TPA |
| Tumor Necrosis Factor | FMA |
| Thyroid Stimulating Hormone α Gene | Thyroid Hormone |

In various embodiments, the human cytomegalovirus (CMV) immediate early gene promoter, the SV40 early promoter and the Rous sarcoma virus long terminal repeat can be used to obtain high-level expression of the polynucleotide of interest. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of the therapeutic gene.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base (EPDB)) could also be used to drive expression of a particular construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. Such polyadenylation signals as that from SV40, bovine growth hormone, and the herpes simplex virus thymidine kinase gene have been found to function well in a number of target cells.

F. Methods of Isolating Adenovirus

Adenoviral infection results in the lysis of the cells being infected. The lytic characteristics of adenovirus infection permit two different modes of virus isolation and production. One is harvesting infected cells prior to cell lysis. The other mode is harvesting virus supernatant after complete cell lysis by the produced virus. For the latter mode, longer incubation times are required in order to achieve complete cell lysis. This prolonged incubation time after virus infection creates a serious concern about increased possibility of generation of replication competent adenovirus (RCA), particularly for the current first generation adenoviral vectors (E1-deleted vector). Therefore, in certain embodiments of the present invention, the methods for producing an adenovirus involve harvesting the host cells and then lysing the host cells. Table 3 lists the most common methods that have been used for lysing cells after cell harvest.

TABLE 3

Methods used for cell lysis

| Methods | Procedures | Comments |
|---|---|---|
| Freeze-thaw | Cycling between dry ice and 37° C. water bath | Easy to carry out at lab scale. High cell lysis efficiency Not scaleable Not recommended for large scale manufacturing |
| Solid Shear | French Press Hughes Press | Capital equipment investment Virus containment concerns Lack of experience |
| Detergent lysis | Non-ionic detergent solutions such as Tween, Triton, NP-40, etc. | Easy to carry out at both lab and manufacturing scale Wide variety of detergent choices Concerns of residual detergent in finished product |
| Hypotonic solution lysis | water, citric buffer | Low lysis efficiency |
| Liquid Shear | Homogenizer Impinging Jet Microfluidizer | Capital equipment investment Virus containment concerns Scaleability concerns |
| Sonication | ultrasound | Capital equipment investment Virus containment concerns Noise pollution Scaleability concern |

1. Detergents

In certain embodiments of the present invention, the methods for producing an adenovirus involve isolating the adenovirus by lysing the host cells with a detergent. Cells are bounded by membranes. In order to release components of the cell, it is necessary to break open the cells. The most advantageous way in which this can be accomplished, according to the present invention, is to solubilize the membranes with the use of detergents. Detergents are amphipathic molecules with an apolar end of aliphatic or aromatic nature and a polar end which may be charged or uncharged. Detergents are more hydrophilic than lipids and thus have greater water solubility than lipids. They allow for the dispersion of water insoluble compounds into aqueous media and are used to isolate and purify proteins in a native form.

Any detergent capable of lysing the host cells is contemplated by the claimed invention. One of skill in the art would be familiar with the wide range of detergents available for lysing cells.

Detergents can be denaturing or non-denaturing. The former can be anionic such as sodium dodecyl sulfate or cationic such as ethyl trimethyl ammonium bromide. These detergents totally disrupt membranes and denature the protein by breaking protein-protein interactions. Non denaturing detergents can be divided into non-anionic detergents such as Triton®X-100, bile salts such as cholates and zwitterionic detergents such as CHAPS. Zwitterionics contain both cationic and anion groups in the same molecule, the positive electric charge is neutralized by the negative charge on the same or adjacent molecule.

Denaturing agents such as SDS bind to proteins as monomers and the reaction is equilibrium driven until saturated. Thus, the free concentration of monomers determines the necessary detergent concentration. SDS binding is cooperative i.e. the binding of one molecule of SDS increase the probability of another molecule binding to that protein, and alters proteins into rods whose length is proportional to their molecular weight.

Non-denaturing agents such as Triton®X-100 do not bind to native conformations nor do they have a cooperative binding mechanism. These detergents have rigid and bulky apolar moieties that do not penetrate into water soluble proteins. They bind to the hydrophobic parts of proteins. Triton®X-100 and other polyoxyethylene nonanionic detergents are inefficient in breaking protein-protein interaction and can cause artifactual aggregations of protein. These detergents will, however, disrupt protein-lipid interactions but are much gentler and capable of maintaining the native form and functional capabilities of the proteins.

Detergent removal can be attempted in a number of ways. Dialysis works well with detergents that exist as monomers. Dialysis is somewhat ineffective with detergents that readily aggregate to form micelles because the micelles are too large to pass through dialysis. Ion exchange chromatography can be utilized to circumvent this problem. The disrupted protein solution is applied to an ion exchange chromatography column and the column is then washed with buffer minus detergent. The detergent will be removed as a result of the equilibration of the buffer with the detergent solution. Alternatively the protein solution may be passed through a density gradient. As the protein sediments through the gradients the detergent will come off due to the chemical potential.

Often a single detergent is not versatile enough for the solubilization and analysis of the milieu of proteins found in a cell. The proteins can be solubilized in one detergent and then placed in another suitable detergent for protein analysis. The protein detergent micelles formed in the first step should separate from pure detergent micelles. When these are added to an excess of the detergent for analysis, the protein is found in micelles with both detergents. Separation of the detergent-protein micelles can be accomplished with ion exchange or gel filtration chromatography, dialysis or buoyant density type separations.

a. Triton®X-Detergents

This family of detergents (Triton®X-100, X114 and NP-40) have the same basic characteristics but are different in their specific hydrophobic-hydrophilic nature. All of these heterogeneous detergents have a branched 8-carbon chain attached to an aromatic ring. This portion of the molecule contributes most of the hydrophobic nature of the detergent. Triton®X detergents are used to solublize membrane proteins under non-denaturing conditions. The choice of detergent to solubilize proteins will depend on the hydrophobic nature of the protein to be solubilized. Hydrophobic proteins require hydrophobic detergents to effectively solubilize them.

Triton®X-100 and NP-40 are very similar in structure and hydrophobicity and are interchangeable in most applications including cell lysis, delipidation protein dissociation and membrane protein and lipid solubilization. Generally 2 mg detergent is used to solubilize 1 mg membrane protein or 10 mg detergent/1 mg of lipid membrane. Triton®X-114 is useful for separating hydrophobic from hydrophilic proteins.

b. Brij® Detergents

These are similar in structure to Triton®X detergents in that they have varying lengths of polyoxyethylene chains attached to a hydrophobic chain. However, unlike Triton®X detergents, the Brij® detergents do not have an aromatic ring and the length of the carbon chains can vary. The Brij® detergents are difficult to remove from solution using dialysis but may be removed by detergent removing gels. Brij®58 is most similar to Triton®X100 in its hydrophobic/hydrophilic characteristics. Brij®-35 is a commonly used detergent in HPLC applications.

c. Dializable Nonionic Detergents $\eta$-Octyl-$\beta$-D-glucoside (octylglucopyranoside) and $\eta$-Octyl-$\beta$-D-thioglucoside (octylthioglucopyranoside, OTG) are nondenaturing nonionic detergents which are easily dialyzed from solution. These detergents are useful for solubilizing membrane proteins and have low UV absorbances at 280 mn. Octylglucoside has a high CMC of 23-25 mM and has been used at concentrations of 1.1-1.2% to solubilize membrane proteins.

Octylthioglucoside was first synthesized to offer an alternative to octylglucoside. Octylglucoside is expensive to manufacture and there are some inherent problems in biological systems because it can be hydrolyzed by $\beta$-glucosidase.

d. Tween® Detergents

The Tween® detergents are nondenaturing, nonionic detergents. They are polyoxyethylene sorbitan esters of fatty acids. Tween® 20 and Tween® 80 detergents are used as blocking agents in biochemical applications and are usually added to protein solutions to prevent nonspecific binding to hydrophobic materials such as plastics or nitrocellulose. They have been used as blocking agents in ELISA and blotting applications. Generally, these detergents are used at concentrations of 0.01-1.0% to prevent nonspecific binding to hydrophobic materials.

Tween® 20 and other nonionic detergents have been shown to remove some proteins from the surface of nitrocellulose. Tween® 80 has been used to solubilize membrane proteins, present nonspecific binding of protein to multiwell plastic tissue culture plates and to reduce nonspecific binding by serum proteins and biotinylated protein A to polystyrene plates in ELISA.

The difference between these detergents is the length of the fatty acid chain. Tween® 80 is derived from oleic acid with a $C_{18}$ chain while Tween® 20 is derived from lauric acid with a $C_{12}$ chain. The longer fatty acid chain makes the Tween® 80 detergent less hydrophilic than Tween® 20 detergent. Both detergents are very soluble in water.

The Tween® detergents are difficult to remove from solution by dialysis, but Tween® 20 can be removed by detergent removing gels. The polyoxyethylene chain found in these detergents makes them subject to oxidation (peroxide formation) as is true with the Triton® X and Brij® series detergents.

e. Zwitterionic Detergents

The zwitterionic detergent, CHAPS, is a sulfobetaine derivative of cholic acid. This zwitterionic detergent is useful for membrane protein solubilization when protein activity is important. This detergent is useful over a wide range of pH (pH 2-12) and is easily removed from solution by dialysis due to high CMCs (8-10 mM). This detergent has low absorbances at 280 nm making it useful when protein monitoring at this wavelength is necessary. CHAPS is compatible with the BCA Protein Assay and can be removed from solution by detergent removing gel. Proteins can be iodinated in the presence of CHAPS.

CHAPS has been successfully used to solubilize intrinsic membrane proteins and receptors and maintain the functional capability of the protein. When cytochrome P-450 is solubilized in either Triton® X-100 or sodium cholate aggregates are formed.

2. Non-Detergent Methods

Various non-detergent methods, though not preferred, may be employed in conjunction with other advantageous aspects of the present invention:

a. Freeze-Thaw

This has been a widely used technique for lysis cells in a gentle and effective manner. Cells are generally frozen rapidly in, for example, a dry ice/ethanol bath until completely frozen, then transferred to a 37° C. bath until completely thawed. This cycle is repeated a number of times to achieve complete cell lysis.

b. Sonication

High frequency ultrasonic oscillations have been found to be useful for cell disruption. The method by which ultrasonic waves break cells is not fully understood but it is known that high transient pressures are produced when suspensions are subjected to ultrasonic vibration. The main disadvantage with this technique is that considerable amounts of heat are generated. In order to minimize heat effects specifically designed glass vessels are used to hold the cell suspension. Such designs allow the suspension to circulate away from the ultrasonic probe to the outside of the vessel where it is cooled as the flask is suspended in ice.

c. High Pressure Extrusion

This is a frequently used method to disrupt microbial cell. The French pressure cell employs pressures of $10.4 \times 10^7$ Pa (16,000 p.s.i) to break cells open. These apparatus consists of a stainless steel chamber which opens to the outside by means of a needle valve. The cell suspension is placed in the chamber with the needle valve in the closed position. After inverting the chamber, the valve is opened and the piston pushed in to force out any air in the chamber. With the valve in the closed position, the chamber is restored to its original position, placed on a solid based and the required pressure is exerted on the piston by a hydraulic press. When the pressure has been attained the needle valve is opened fractionally to slightly release the pressure and as the cells expand they burst. The valve is kept open while the pressure is maintained so that there is a trickle of ruptured cell which may be collected.

d. Solid Shear Methods

Mechanical shearing with abrasives may be achieved in Mickle shakers which oscillate suspension vigorously (300-3000 time/min) in the presence of glass beads of 500 nm diameter. This method may result in organelle damage. A more controlled method is to use a Hughes press where a piston forces most cells together with abrasives or deep frozen paste of cells through a 0.25 mm diameter slot in the pressure chamber. Pressures of up to $5.5 \times 10^7$ Pa (8000 p.s.i.) may be used to lyse bacterial preparations.

e. Liquid Shear Methods

These methods employ blenders, which use high speed reciprocating or rotating blades, homogenizers which use an upward/downward motion of a plunger and ball and microfluidizers or impinging jets which use high velocity passage through small diameter tubes or high velocity impingement of two fluid streams. The blades of blenders are inclined at different angles to permit efficient mixing. Homogenizers are usually operated in short high speed bursts of a few seconds to minimize local heat. These techniques are not generally suitable for microbial cells but even very gentle liquid shear is usually adequate to disrupt animal cells.

f. Hypotonic/Hypertonic Methods

Cells are exposed to a solution with a much lower (hypotonic) or higher (hypertonic) solute concentration. The difference in solute concentration creates an osmotic pressure gradient. The resulting flow of water into the cell in a hypotonic environment causes the cells to swell and burst. The flow of water out of the cell in a hypertonic environment causes the cells to shrink and subsequently burst.

G. Methods of Concentration and Filtration

The present invention involve methods of producing an adenovirus that involve isolating the adenovirus. Methods of isolating the adenovirus from host cells include any methods known to those of skill in the art. For example, these methods may include clarification, concentration and diafiltration. One step in the purification process can include clarification of the cell lysate to remove large particulate matter, particularly cellular components, from the cell lysate. Clarification of the lysate can be achieved using a depth filter or by tangential flow filtration. In one embodiment of the present invention, the cell lysate is concentrated. Concentrating the crude cell lysate may include any step known to those of skill in the art. For example, the crude cell lysate may be passed through a depth filter, which consists of a packed column of relatively non-adsorbent material (e.g. polyester resins, sand, diatomeceous earth, colloids, gels, and the like). In tangential flow filtration (TFF), the lysate solution flows across a membrane surface which facilitates back diffusion of solute from the membrane surface into the bulk solution. Membranes are generally arranged within various types of filter apparatus including open channel plate and frame, hollow fibers, and tubules.

After clarification and prefiltration of the cell lysate, the resultant virus supernatant may be concentrated and buffer may be exchanged by diafiltration. The virus supernatant can be concentrated by tangential flow filtration across an ultrafiltration membrane of 100-300 K nominal molecular weight cutoff. Ultrafiltration is a pressure-modified convective process that uses semi-permeable membranes to separate species by molecular size, shape and/or charge. It separates solvents from solutes of various sizes, independent of solute molecular size. Ultrafiltration is gentle, efficient and can be used to simultaneously concentrate and desalt solutions. Ultrafiltration membranes generally have two distinct layers: a thin (0.1-1.5 μm), dense skin with a pore diameter of 10-400 angstroms and an open substructure of progressively larger voids which are largely open to the permeate side of the ultrafilter. Any species capable of passing through the pores of the skin can therefore freely pass through the membrane. For maximum retention of solute, a membrane is selected that has a nominal molecular weight cut-off well below that of the species being retained. In macromolecular concentration, the membrane enriches the content of the desired biological species and provides filtrate cleared of retained substances. Microsolutes are removed convectively with the solvent. As concentration of the retained solute increases, the ultrafiltration rate diminishes.

Some embodiments of the present invention involve use of exchanging buffer of the crude cell lysate. Buffer exchange, or diafiltration, involves using ultrafilters is an ideal way for removal and exchange of salts, sugars, non-aqueous solvents separation of free from bound species, removal of material of low molecular weight, or rapid change of ionic and pH environments. Microsolutes are removed most efficiently by adding solvent to the solution being ultrafiltered at a rate equal to the ultrafiltration rate. This washes microspecies from the solution at constant volume, purifying the retained species.

H. Removing Nucleic Acid Contaminants

Certain embodiments of the methods for producing an adenovirus involve reducing the concentration of contaminating nucleic acids in a crude cell lysate. The present invention employs nucleases to remove contaminating nucleic acids. Exemplary nucleases include Benzonase®, Pulmozyme®; or any other DNase or RNase commonly used within the art.

Enzymes such as Benzonaze® degrade nucleic acid and have no proteolytic activity. The ability of Benzonase® to rapidly hydrolyze nucleic acids makes the enzyme ideal for reducing cell lysate viscosity. It is well known that nucleic acids may adhere to cell derived particles such as viruses. The adhesion may interfere with separation due to agglomeration, change in size of the particle or change in particle charge, resulting in little if any product being recovered with a given purification scheme. Benzonase® is well suited for reducing the nucleic acid load during purification, thus eliminating the interference and improving yield.

As with all endonucleases, Benzonase® hydrolyzes internal phosphodiester bonds between specific nucleotides. Upon complete digestion, all free nucleic acids present in solution are reduced to oligonucleotides 2 to 4 bases in length.

I. Purification Techniques

Certain embodiments of the invention involve methods for producing an adenovirus that include purifying the adenovirus. The adenovirus generated in the claimed methods can be purified by any method known to those of skill in the art. In certain embodiments, specific purification techniques are employed. These techniques are delineated as follows.

1. Density Gradient Centrifugation

There are two methods of density gradient centrifugation, the rate zonal technique and the isopycnic (equal density) technique, and both can be used when the quantitative separation of all the components of a mixture of particles is required. They are also used for the determination of buoyant densities and for the estimation of sedimentation coefficients.

Particle separation by the rate zonal technique is based upon differences in size or sedimentation rates. The technique involves carefully layering a sample solution on top of a performed liquid density gradient, the highest density of which exceeds that of the densest particles to be separated. The sample is then centrifuged until the desired degree of separation is effected, i.e., for sufficient time for the particles to travel through the gradient to form discrete zones or bands which are spaced according to the relative velocities of the particles. Since the technique is time dependent, centrifugation must be terminated before any of the separated zones pellet at the bottom of the tube. The method has been used for the separation of enzymes, hormones, RNA-DNA hybrids, ribosomal subunits, subcellular organelles, for the analysis of size distribution of samples of polysomes and for lipoprotein fractionations.

The sample is layered on top of a continuous density gradient which spans the whole range of the particle densities which are to be separated. The maximum density of the gradient, therefore, must always exceed the density of the most dense particle. During centrifugation, sedimentation of the particles occurs until the buoyant density of the particle and the density of the gradient are equal (ie., where $p_p=p_m$ in equation 2.12). At this point no further sedimentation occurs, irrespective of how long centrifugation continues, because the particles are floating on a cushion of material that has a density greater than their own.

Isopycnic centrifugation, in contrast to the rate zonal technique, is an equilibrium method, the particles banding to form zones each at their own characteristic buoyant density. In cases where, perhaps, not all the components in a mixture of particles are required, a gradient range can be selected in which unwanted components of the mixture will sediment to the bottom of the centrifuge tube whilst the particles of interest sediment to their respective isopycnic positions. Such a technique involves a combination of both the rate zonal and isopycnic approaches.

Isopycnic centrifugation depends solely upon the buoyant density of the particle and not its shape or size and is independent of time. Hence soluble proteins, which have a very similar density (e.g., $p=1.3$ g cm$^{-3}$ in sucrose solution), cannot usually be separated by this method, whereas subcellular organelles (e.g., Golgi apparatus, $p=1.11$ g cm$^{-3}$, mitochondria, $p=1.19$ g cm$^{-3}$ and peroxisomes, $p=1.23$ g cm$^{-3}$ in sucrose solution) can be effectively separated.

As an alternative to layering the particle mixture to be separated onto a preformed gradient, the sample is initially mixed with the gradient medium to give a solution of uniform density, the gradient 'self-forming', by sedimentation equilibrium, during centrifugation. In this method (referred to as the equilibrium isodensity method), use is generally made of the salts of heavy metals (e.g., caesium or rubidium), sucrose, colloidal silica or Metrizamide.

The sample (e.g., DNA) is mixed homogeneously with, for example, a concentrated solution of caesium chloride. Centrifugation of the concentrated caesium chloride solution results in the sedimentation of the CsCl molecules to form a concentration gradient and hence a density gradient. The sample molecules (DNA), which were initially uniformly distributed throughout the tube now either rise or sediment until they reach a region where the solution density is equal to their own buoyant density, i.e. their isopycnic position, where they will band to form zones. This technique suffers from the disadvantage that often very long centrifugation times (e.g., 36 to 48 hours) are required to establish equilibrium. However, it is commonly used in analytical centrifugation to determine the buoyant density of a particle, the base composition of double stranded DNA and to separate linear from circular forms of DNA.

Many of the separations can be improved by increasing the density differences between the different forms of DNA by the incorporation of heavy isotopes (e.g., $^{15}$N during biosynthesis, a technique used by Leselson and Stahl to elucidate the mechanism of DNA replication in *Esherichia coli*, or by the binding of heavy metal ions or dyes such as ethidium bromide. Isopycnic gradients have also been used to separate and purify viruses and analyze human plasma lipoproteins.

2. Chromatography

In certain embodiments of the invention, adenovirus will be purified using chromatography. The adenovirus may be subjected to one or more chromatography steps. Purification techniques are well known to those of skill in the art. These techniques tend to involve the fractionation of the cellular milieu to separate the adenovirus particles from other components of the mixture. Having separated adenoviral particles from the other components, the adenovirus may be purified using chromatographic and electrophoretic techniques to achieve complete purification. Analytical methods particularly suited to the preparation of a pure adenovrial particle of the present invention are ion-exchange chromatography, size exclusion chromatography; polyacrylamide gel electrophoresis. A particularly efficient purification method to be employed in conjunction with the present invention is HPLC.

Certain aspects of the present invention concern the purification, and in particular embodiments, the substantial purification, of an adenoviral particle. The term "purified" as used herein, is intended to refer to a composition, isolatable from other components, wherein the adenoviral particle is purified to any degree relative to its naturally-obtainable form. A purified adenoviral particle therefore also refers to an adenoviral component, free from the environment in which it may naturally occur.

Generally, "purified" will refer to an adenoviral particle that has been subjected to fractionation to remove various other components, and which composition substantially retains its expressed biological activity. Where the term "substantially purified" is used, this designation will refer to a composition in which the particle, protein or peptide forms the major component of the composition, such as constituting about 50% or more of the constituents in the composition.

Various methods for quantifying the degree of purification of a protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

There is no general requirement that the adenovirus, always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater -fold purification than the same technique utilizing a low pressure chromatography system. Methods exhibiting a lower degree of relative purification may have advantages in total recovery of protein product, or in maintaining the activity of an expressed protein.

Of course, it is understood that the chromatographic techniques and other purification techniques known to those of skill in the art may also be employed to purify proteins expressed by the adenoviral vectors of the present invention. Ion exchange chromatography and high performance liquid chromatography are exemplary purification techniques employed in the purification of adenoviral particles and are described in further detail herein below.

Ion-Exchange Chromatography. The basic principle of ion-exchange chromatography is that the affinity of a substance for the exchanger depends on both the electrical properties of the material and the relative affinity of other charged substances in the solvent. Hence, bound material can be eluted by changing the pH, thus altering the charge of the material, or by adding competing materials, of which salts are but one example. Because different substances have different electrical properties, the conditions for release vary with each bound molecular species. In general, to get good separation, the methods of choice are either continuous ionic strength gradient elution or stepwise elution. (A gradient of pH alone is not often used because it is difficult to set up a pH gradient without simultaneously increasing ionic strength.) For an anion exchanger, either pH and ionic strength are gradually increased or ionic strength alone is increased. For a cation exchanger, both pH and ionic strength are increased. The actual choice of the elution procedure is usually a result of trial and error and of considerations of stability. For example, for unstable materials, it is best to maintain fairly constant pH.

An ion exchanger is a solid that has chemically bound charged groups to which ions are electrostatically bound; it can exchange these ions for ions in aqueous solution. Ion exchangers can be used in column chromatography to separate molecules according to charge; actually other features of the molecule are usually important so that the chromatographic behavior is sensitive to the charge density, charge distribution, and the size of the molecule.

The principle of ion-exchange chromatography is that charged molecules adsorb to ion exchangers reversibly so that molecules can be bound or eluted by changing the ionic environment. Separation on ion exchangers is usually accomplished in two stages: first, the substances to be separated are bound to the exchanger, using conditions that give stable and tight binding; then the column is eluted with buffers of different pH, ionic strength, or composition and the components of the buffer compete with the bound material for the binding sites.

An ion exchanger is usually a three-dimensional network or matrix that contains covalently linked charged groups. If a group is negatively charged, it will exchange positive ions and is a cation exchanger. A typical group used in cation exchangers is the sulfonic group, $SO_3^-$. If an $H^+$ is bound to the group, the exchanger is said to be in the acid form; it can, for example, exchange one $H^+$ for one $Na^+$ or two $H^+$ for one $Ca^{2+}$. The sulfonic acid group is called a strongly acidic cation exchanger. Other commonly used groups are phenolic hydroxyl and carboxyl, both weakly acidic cation exchangers. If the charged group is positive—for example, a quaternary amino group—it is a strongly basic anion exchanger. The most common weakly basic anion exchangers are aromatic or aliphatic amino groups.

The matrix can be made of various material. Commonly used materials are dextran, cellulose, agarose and copolymers of styrene and vinylbenzene in which the divinylbenzene both cross-links the polystyrene strands and contains the charged groups. Table 4 gives the composition of many ion exchangers.

The total capacity of an ion exchanger measures its ability to take up exchangeable groups per milligram of dry weight. This number is supplied by the manufacturer and is important because, if the capacity is exceeded, ions will pass through the column without binding.

TABLE 4

| Matrix | Exchanger | Functional Group | Tradename |
|---|---|---|---|
| Dextran | Strong Cationic | Sulfopropyl | SP-Sephadex |
| | Weak Cationic | Carboxymethyl | CM-Sephadex |
| | Strong Anionic | Diethyl-(2-hydroxypropyl)-aminoethyl | QAE-Sephadex |
| | Weak Anionic | Diethylaminoethyl | DEAE-Sephadex |
| Cellulose | Cationic | Carboxymethyl | CM-Cellulose |
| | Cationic | Phospho | P-cel |
| | Anionic | Diethylaminoethyl | DEAE-cellulose |
| | Anionic | Polyethylenimine | PEI-Cellulose |
| | Anionic | Benzoylated-naphthoylated, deiethylaminoethyl | DEAE(BND)-cellulose |
| | Anionic | p-Aminobenzyl | PAB-cellulose |
| Styrenedivinylbenzene | Strong Cationic | Sulfonic acid | AG 50 |
| | Strong Anionic | | AG 1 |
| | Strong Cationic + Strong Anionic | Sulfonic acid + Tetramethylammonium | AG 501 |
| Acrylic | Weak Cationic | Carboxylic | Bio-Rex 70 |
| Phenolic | Strong Cationic | Sulfonic acid | Bio-Rex 40 |
| Expoxyamine | Weak Anionic | Tertiary amino | AG-3 |

The available capacity is the capacity under particular experimental conditions (i.e., pH, ionic strength). For example, the extent to which an ion exchanger is charged depends on the pH (the effect of pH is smaller with strong ion exchangers). Another factor is ionic strength because small ions near the charged groups compete with the sample molecule for these groups. This competition is quite effective if the sample is a macromolecule because the higher diffusion coefficient of the small ion means a greater number of encounters. Clearly, as buffer concentration increases, competition becomes keener.

The porosity of the matrix is an important feature because the charged groups are both inside and outside the matrix and because the matrix also acts as a molecular sieve. Large molecules may be unable to penetrate the pores; so the capacity will decease with increasing molecular dimensions. The porosity of the polystyrene-based resins is determined by the amount of cross-linking by the divinylbenzene (porosity decreases with increasing amounts of divinylbenzene). With the Dowex and AG series, the percentage of divinylbenzene is indicated by a number after an X—hence, Dowex 50-X8 is 8% divinylbenzene.

Ion exchangers come in a variety of particle sizes, called mesh size. Finer mesh means an increased surface-to-volume ration and therefore increased capacity and decreased time for exchange to occur for a given volume of the exchanger. On the other hand, fine mesh means a slow flow rate, which can increase diffusional spreading. The use of very fine particles, approximately 10 μm in diameter and high pressure to maintain an adequate flow is called high-performance or high-pressure liquid chromatography or simply HPLC. Such a collection of exchangers having such different properties—charge, capacity, porosity, mesh—makes the selection of the appropriate one for accomplishing a particular separation difficult.

There are a number of choice to be made when employing ion exchange chromatography as a technique. The first choice to be made is whether the exchanger is to be anionic or cationic. If the materials to be bound to the column have a single charge (i.e., either plus or minus), the choice is clear. However, many substances (e.g., proteins, viruses), carry both negative and positive charges and the net charge depends on the pH. In such cases, the primary factor is the stability of the substance at various pH values. Most proteins have a pH range of stability (i.e., in which they do not denature) in which they are either positively or negatively charged. Hence, if a protein is stable at pH values above the isoelectric point, an anion exchanger should be used; if stable at values below the isoelectric point, a cation exchanger is required.

The choice between strong and weak exchangers is also based on the effect of pH on charge and stability. For example, if a weakly ionized substance that requires very low or high pH for ionization is chromatographed, a strong ion exchanger is called for because it functions over the entire pH range. However, if the substance is labile, weak ion exchangers are preferable because strong exchangers are often capable of distorting a molecule so much that the molecule denatures. The pH at which the substance is stable must, of course, be matched to the narrow range of pH in which a particular weak exchanger is charged. Weak ion exchangers are also excellent for the separation of molecules with a high charge from those with a small charge, because the weakly charged ions usually fail to bind. Weak exchangers also show greater resolution of substances if charge differences are very small. If a macromolecule has a very strong charge, it may be impossible to elute from a strong exchanger and a weak exchanger again may be preferable. In general, weak exchangers are more useful than strong exchangers.

The Sephadex and Bio-gel exchangers offer a particular advantage for macromolecules that are unstable in low ionic strength. Because the cross-links in these materials maintain the insolubility of the matrix even if the matrix is highly polar, the density of ionizable groups can be made several times greater than is possible with cellulose ion exchangers. The increased charge density means increased affinity so that adsorption can be carried out at higher ionic strengths. On the other hand, these exchangers retain some of their molecular sieving properties so that sometimes molecular weight differences annul the distribution caused by the charge differences; the molecular sieving effect may also enhance the separation.

Small molecules are best separated on matrices with small pore size (high degree of cross-linking) because the available capacity is large, whereas macromolecules need large pore size. However, except for the Sephadex type, most ion exchangers do not afford the opportunity for matching the porosity with the molecular weight.

The cellulose ion exchangers have proved to be the best for purifying large molecules such as proteins and polynucleotides. This is because the matrix is fibrous, and hence all functional groups are on the surface and available to even the largest molecules. In many cases however, beaded forms such as DEAE-Sephacel and DEAE-Biogel P are more useful because there is a better flow rate and the molecular sieving effect aids in separation.

Selecting a mesh size is always difficult. Small mesh size improves resolution but decreases flow rate, which increases zone spreading and decreases resolution. Hence, the appropriate mesh size is usually determined empirically.

Because buffers themselves consist of ions, they can also exchange, and the pH equilibrium can be affected. To avoid these problems, the rule of buffers is adopted: use cationic buffers with anion exchangers and anionic buffers with cation exchangers. Because ionic strength is a factor in binding, a buffer should be chosen that has a high buffering capacity so that its ionic strength need not be too high. Furthermore, for best resolution, it has been generally found that the ionic conditions used to apply the sample to the column (the so-called starting conditions) should be near those used for eluting the column.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

In certain embodiments of the present invention the methods of producing an adenovirus will involve methods to analyze virus production. Any method known to those of skill in the art can be used to analyze virus production. In a certain embodiment, virus production is analyzed using HPLC.

J. Pharmaceutical Formulations

The present invention includes, in certain embodiments, methods for producing an adenovirus that involve placing the adenovirus into a pharmaceutically acceptable composition. The present invention also includes compositions of adenovirus prepared by one of the processes disclosed herein, wherein the composition is a pharmaceutically acceptable composition.

The phrase "pharmaceutically acceptable composition" refers to molecular entities and compositions that do not produce an adverse, allergic or other untoward reaction when administered to an animal, or a human, as appropriate. As used herein, "pharmaceutically acceptable composition" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients also can be incorporated into the composition. In addition, the composition can include supplementary inactive ingredients. For instance, the composition for use as a mouthwash may include a flavorant or the composition may contain supplementary ingredients to make the formulation timed-release.

Aqueous compositions of the present invention comprise an effective amount of the expression cassette, dissolved or dispersed in a pharmaceutically acceptable carrier or acqueous medium. Such compositions also are referred to as inocula. Examples of aqueous compositions include a formulation for intravenous administration or a formulation for topical application.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The adenovirus preparations of the present invention may include classic pharmaceutical preparations. Administration of therapeutic compositions according to the present invention will be via any common route so long as the target tissue is available via that route. Such compositions would normally be administered as pharmaceutically acceptable compositions that include physiologically acceptable carriers, buffers or other excipients.

The therapeutic and preventive compositions of the present invention are advantageously administered in the form of invention liquid solutions or suspensions; solid forms suitable for solution in, or suspension in, liquid prior to topical use may also be prepared. A typical composition for such purpose comprises a pharmaceutically acceptable carrier. For instance, the composition may contain 10 mg, 25 mg, 50 mg or up to about 100 mg of human serum albumin per ml of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Preservatives include antimicrobial agents, anti-oxidants, chelating agents and inert gases. The pH and exact concentration of the various components of the pharmaceutical composition are adjusted according to well-known parameters.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions such as mouthwashes and mouthrinses, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25-60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

For oral administration the expression cassette of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

One may also use solutions and/or sprays, hyposprays, aerosols and/or inhalants in the present invention for administration. One example is a spray for administration to the aerodigestive tract. The sprays are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation. Additional formulations which are suitable for other modes of administration include vaginal or rectal suppositories and/or pessaries. Formulations for other types of administration that is topical include, for example, a cream, suppository, ointment or salve.

K. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A study to evaluate the effect of infection temperature on adenovirus production was conducted using two adenoviral vectors, Adp53 and Admda7.

Four temperatures were evaluated: 32° C., 35° C., 37° C., and 39° C. The adenoviral vector used were Adp53 and Admda7. The cells were HEK293 cells (cell passage #54). The experiments were carried out in 293 cells grown in T-150 flasks (Corning) using an incubator (Form a Scientific, Inc., model # Steri-Cult 200). The infection medium was DMEM+ 2% FBS. The multiplicity of infection (MOI) was 150 vp/cell.

Nine T-150 flasks were seeded with 293 cells (cell passage# 54) at seeding density of $5.8 \times 10^4$ cells/cm$^2$ in 10% FBS-DMEM medium. All flasks were placed inside a 37° C. incubator with 10% $CO_2$, 95% relative humidity. After 72 hrs post-seeding, one flask was trypsinized and counted, and the cell density was $1.6 \times 10^5$ cells/cm$^2$. Spent medium from the remaining eight flasks was aspirated and fresh 2% FBS-DMEM was added. The flasks were infected with Adp53 or Admda7 at MOI of 150 vp/cell based on the cell count of the trypsinized flask above. Two of the flasks were placed inside incubators at each of the following temperatures: 39° C., 37° C., 35° C. and 32° C. All incubators were set at 10% $CO_2$ and 95% relative humidity environment. The temperatures of all the incubators were calibrated using a temperature calibration equipment (Kaye Instruments) prior to use to ensure the accuracy of the different temperatures. Ninety-six hours post-infection, all the flasks were harvested. Tween20 was added into each flask to a final concentration of 1%(v/v) and the flasks were incubated for 30 mins at 37° C. Benzonase (EMD Chemicals) was then added to 100 u/ml for 1 hr at 37° C. A sample was taken from each flask for HPLC analysis of virus concentration.

Figure 1B:
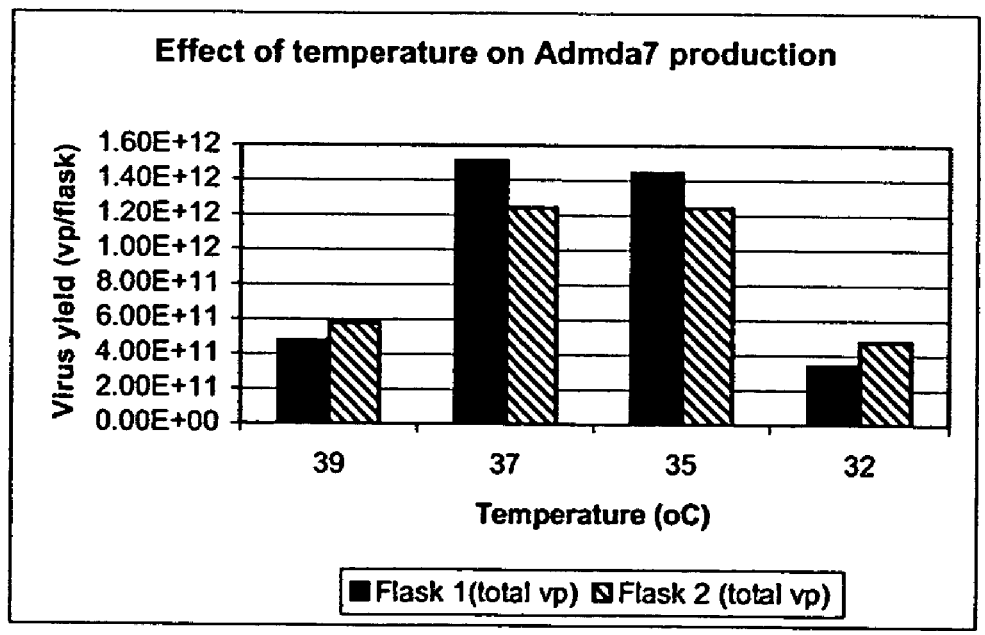
FIG. 1B shows results of a study demonstrating the effect of temperature on Admda7 production (vp/flask).

The results for Adp53 and Admda7 are shown in FIG. 1A and FIG. 1B, respectively.

Virus production was reduced significantly at 39° C. relatively to 37° C. (FIG. 1A and FIG. 1B). At an infection temperature of 37° C., Admda7 virus yield was 2.6E10 vp/ml or 26,000 vp/cell. At an infection temperature of 35° C., Ad-mda7 virus yield was 4.1E10 vp/ml or 41,000 vp/cell. Approximately equivalent virus production was attained at both 37° C. and 35° C. Virus production at 32° C. was much lower than that at 37° C. The same general conclusion was reached for both Adp53 and Admda7 vectors.

The optimal infection temperature for adenovirus production is in the range of greater than 32° C. and less than 37° C. The results also demonstrated the detrimental effect of high infection temperature (39° C.) on adenovirus production.

Example 2

Materials and Methods

| | |
|---|---|
| Bioreactor model: | 20/50EH (Wave Biotech, LLC) |
| Culture medium: | CD293 protein free medium (Invitrogen ™) |
| HEK293 suspension cells: | Adapted to serum-free suspension culture at Introgen Therapeutics, Inc. |
| Adenoviral vectors: | Supplied by Introgen Therapeutics, Inc. |
| YSI biochemistry analyzer: | YSI-2700 SELECT ™ |

Cell Growth and Adenoviral Vector Production Without Medium Perfusion

An adenoviral vector production run was carried out in a 10 L (5 L working volume) Wave Bioreactor®. HEK293 suspension cells were seeded at 4.8E5 cells/ml and were allowed to grow to 1.2E6 cells/ml in protein-free CD293 medium. The rocking speed was set at 10 and the rocking angle was set at 11. The culture pH was maintained by adjusting $CO_2$ gas percentage delivered by the gas mixer. The dissolved oxygen tension (DOT) in the culture medium was monitored using a disposable DOT probe supplied by Wave Biotech™.

Figure 2:
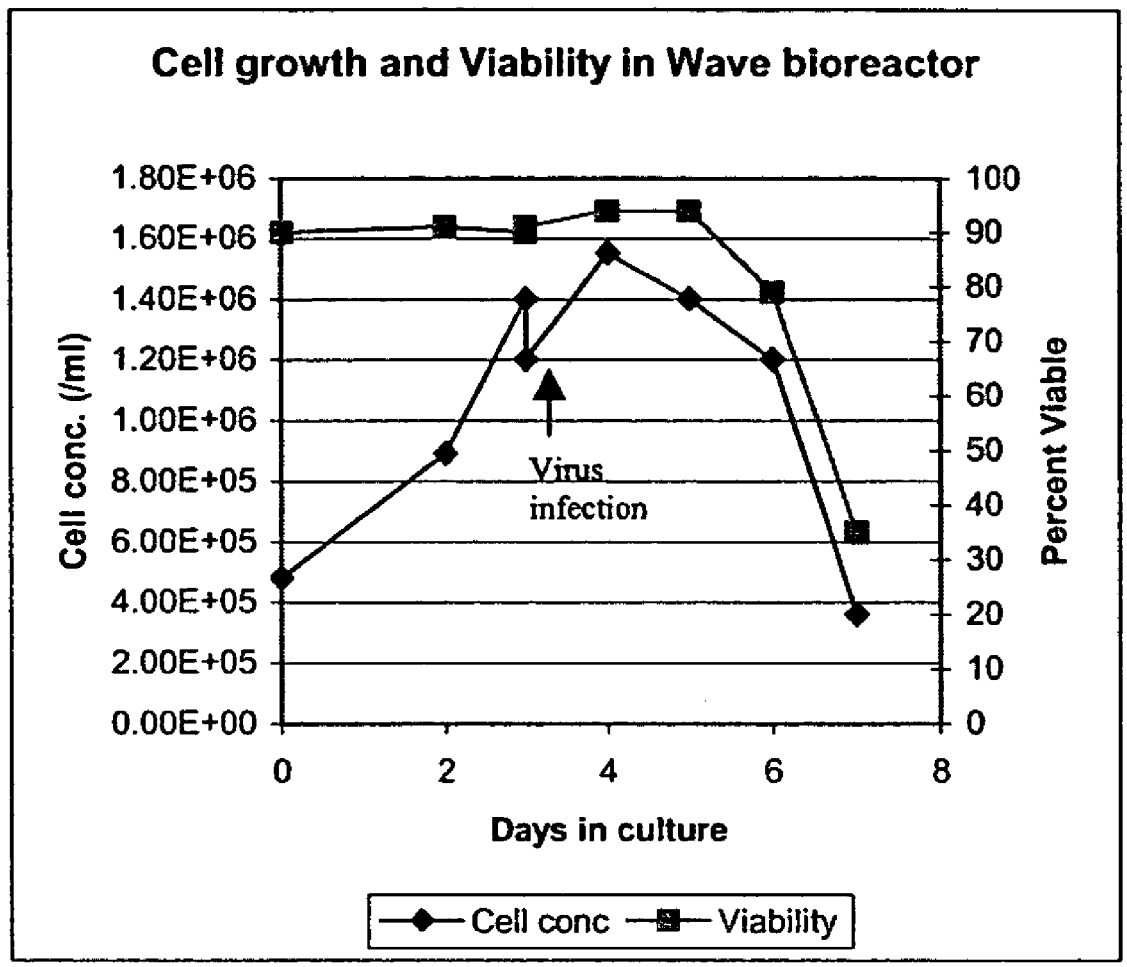
FIG. 2. Cell growth and viability in the bioreactor.
Figure 3:
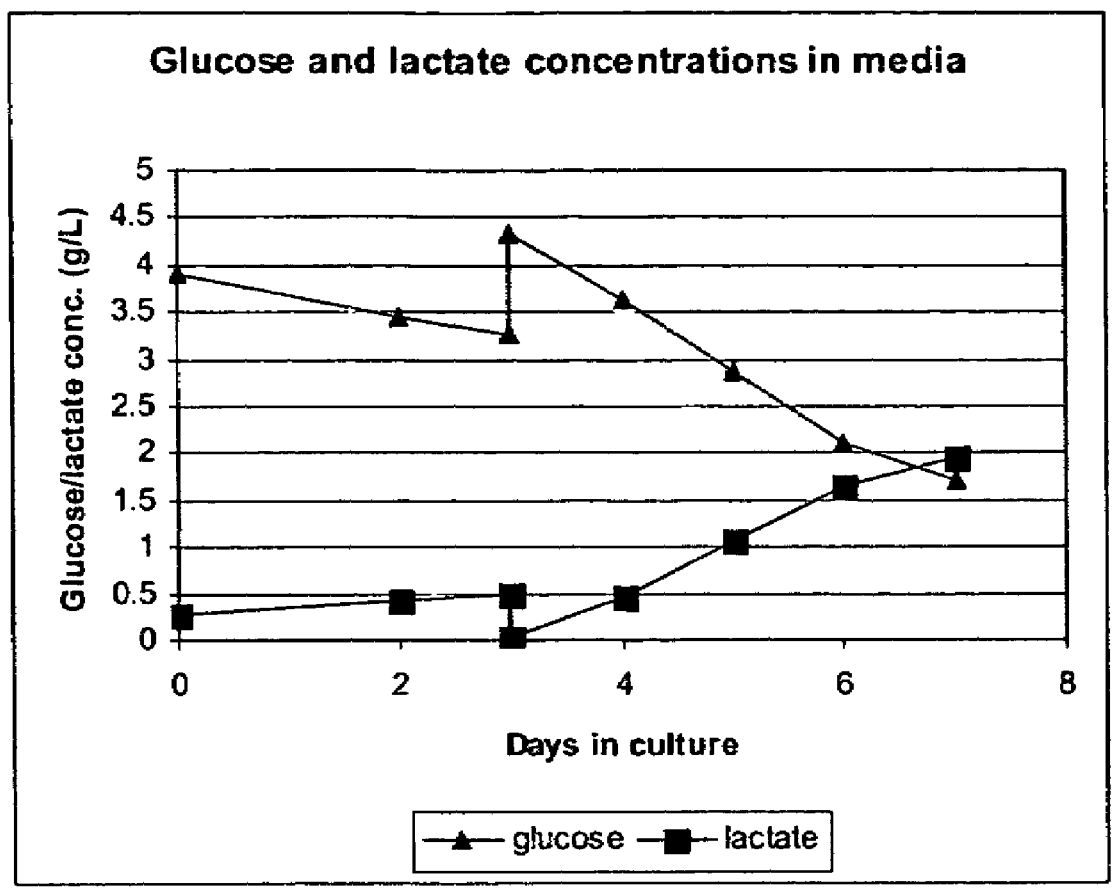
FIG. 3. Glucose and lactate concentrations (g/L) in media vs. days in culture.

When the cell concentration reached 1.2E6 cells/ml, the culture was transferred out of the bioreactor, centrifuged, and the resulting cell pellet was resuspended with fresh CD293 medium. The cell suspension was transferred back into the bioreactor and the cells were infected with an adenoviral vector at a MOI of 50 vp/cell. Infection was allowed to proceed for 4 days. The culture was harvested on day 4 post-infection. The cell growth data are shown in FIG. 2. FIG. 2 demonstrates that cell concentration peaked at day 4, and viability remained steady but showed decline after day 5. FIG. 3 shows nutrient/metabolite data. Following virus infection, glucose concentration declined over time, and lactate concentration increased over time.

Adenoviral vector production was measured using an anion exchange HPLC method. The adenoviral vector concentration in the bioreactor was found to be 4.5E10 vp/ml, and the cell-specific vector productivity was 37,000 vp/cell. The vector productivity is in close agreement with those seen using the parental anchorage dependent HEK293 cells in serum-containing media.

Example 3

Figure 4:
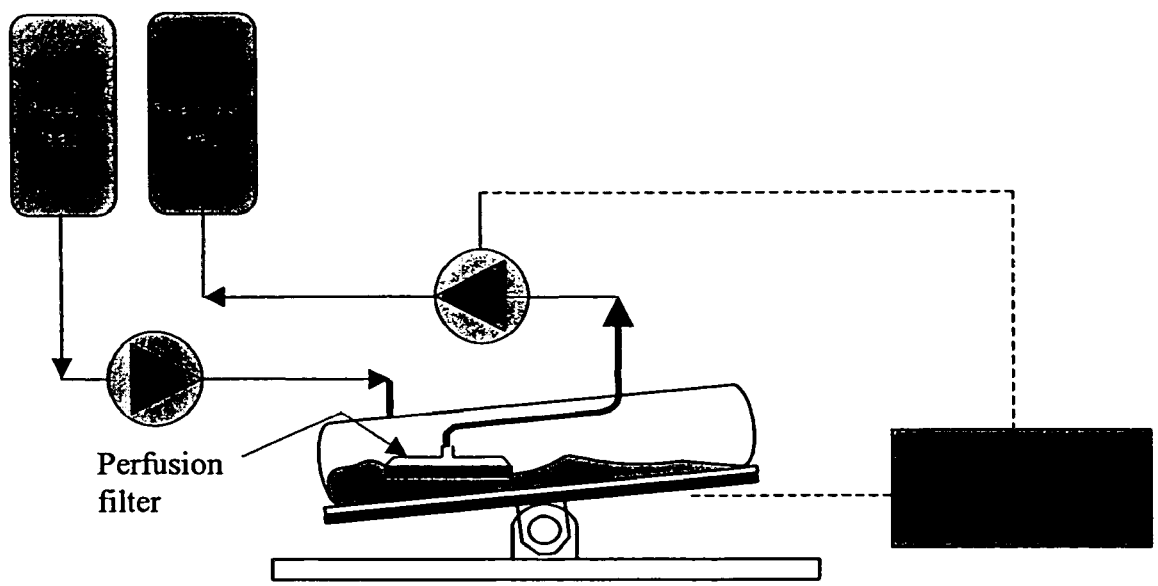
FIG. 4. Diagram of a perfusion bioreactor system.

Cell Growth and Adenoviral Vector Production With Perfusion During the Cell Growth Phase A uniquely designed perfusion Wave bioreactor was set up as shown in FIG. 4. The system shown in FIG. 4 utilizes an internal flat filter to provide separation between the cells and spent medium. Spent culture medium is withdrawn through the floating filter. No medium recirculation is required, and consequently this mode of medium perfusion is very gentle to the cells in culture. The wave action minimizes filter clogging during perfusion. The culture volume during perfusion is maintained by a load cell used to trigger fresh medium addition.

Figure 5:
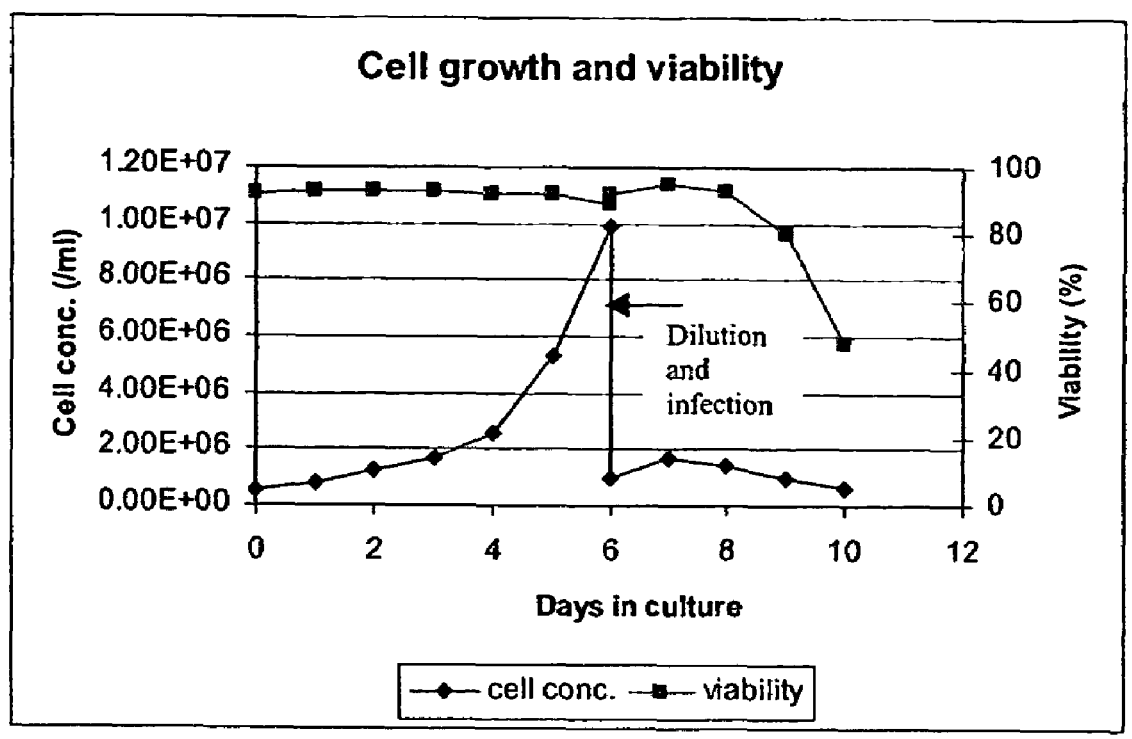
FIG. 5. Cell growth and viability in perfusion culture vs. days in culture.
Figure 6:
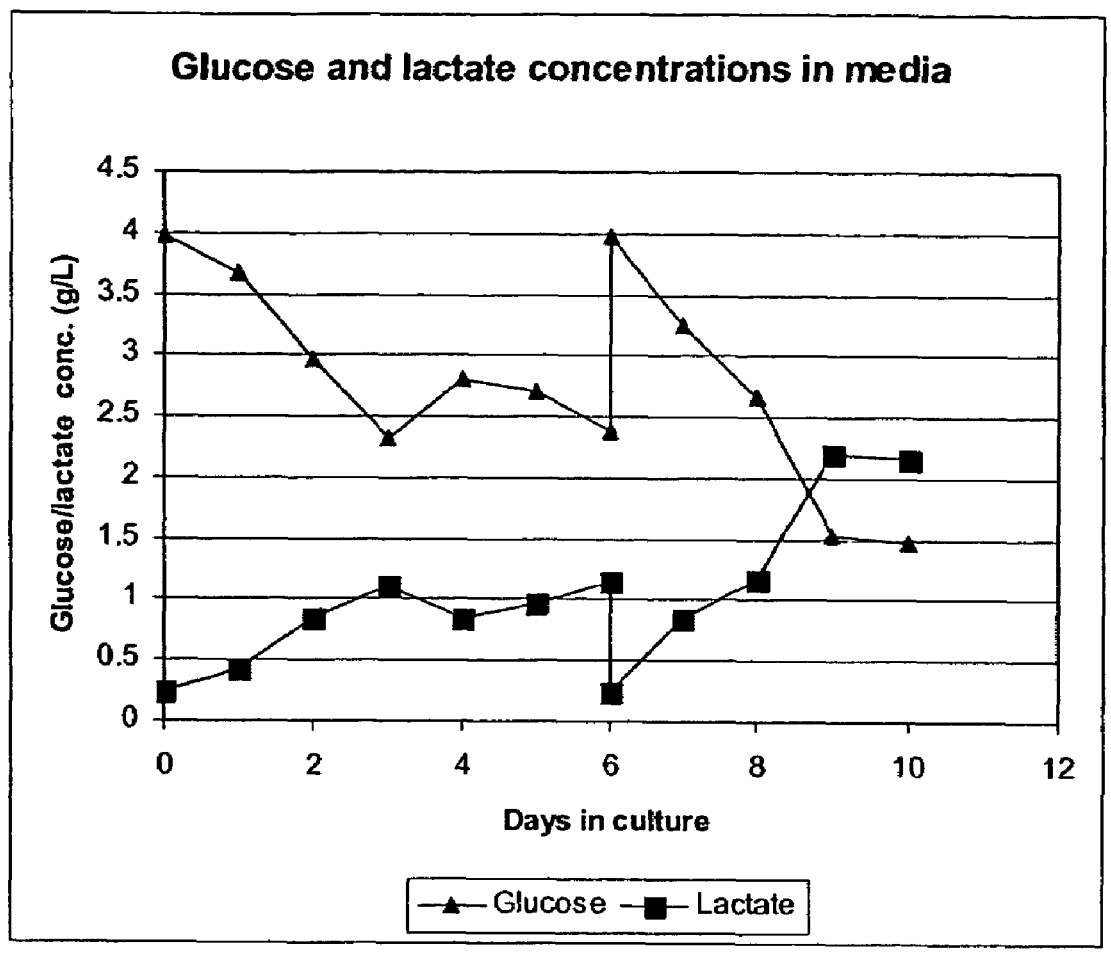
FIG. 6. Glucose and lactate concentrations (g/L) in perfusion culture vs. days in culture.

A 1 L (working volume) perfusion Wave bioreactor was used to increase the cell concentration in the growth phase prior to virus infection. The cell growth and nutrient/metabolite concentrations during culture are shown in FIG. 5 and FIG. 6.

HEK293 suspension cells were seeded at a cell concentration of 5E5 cells/ml. On day 3 of culture, medium perfusion was started at a cell concentration of 1.7E6 cells/ml. Cell concentration increased approximately exponentially to 1E7 cells/ml on day 6, and cell viability was maintained above 90%. The culture was diluted 10-fold with fresh CD293 medium to supplement nutrients and dilute potentially toxic metabolites. The culture was immediately infected with an adenoviral vector at a MOI of 50 vp/cell in a larger Wave Bioreactor™ without a perfusion filter. Medium perfusion was not resumed after virus infection. The infection was allowed to proceed for 4 days. The culture was harvested on day 4 post-virus infection.

The adenoviral vector production was measured by an anion exchange HPLC method. The adenoviral vector concentration in the Wave Bioreactor® was 3.5E10 vp/ml, and the cell-specific vector productivity was 35,000 vp/cell.

These results demonstrate satisfactory adenoviral vector production in a suspension of HEK293 cells grown in a protein-free CD293 medium in the Wave bioreactor. The efficient and scalable perfusion-dilution method overcomes the difficulties associated with medium exchange at the time of virus infection for suspension cultures. Approximately equivalent virus productivity was attained with the perfusion-dilution infection method relative to the centrifugation complete medium exchange infection method. The ease of operation of the perfusion-dilution infection method makes it the preferred adenoviral vector production method in large scale serum free suspension cultures.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,352,883
U.S. Pat. No. 5,670,488
U.S. Pat. No. 5,932,210
U.S. Pat. No. 5,824,544
U.S. Patent Ser. No. 60/026,667
U.S. Patent Ser. No. 60/203,078
Aboud et al., *Arch. Virol.*, 71:185-195, 1982.
Batra et al., *Am. J. Respir. Cell Mol. Biol.*, 21(2):238-45, 1999.
Berg, *Biotechniques*, 14(6):972-978, 1993.
Blackwell et al., *Arch. Otolaryngol. Head. Neck Surg.*, 125(8):856-863, 1999.
Brett et al., *J. Immunol.*, 150:2869-2884, 1993.
Chillon et al., *J. Virol.*, 73(3):2537-40, 1999.
Chroboczek et al., *Virology*, 186:280-285, 1992.
Cristiano et al., *Cancer Detect. Prev.*, 22(5):445-454, 1998.
Crooks et al., *J Chromatogr.*, 502(1):59-68, 1990.
Dorai et al., *Int. J. Cancer*, 82(6):846-52, 1999.
Feldman et al., *Cardiovasc. Res.*, 32(2):194-207, 1996.
Garnier et al., *Cytotechnology*, 15(1-3):145-155, 1994.
Golasten et al, *New Engl. J. Med.*, 309(11983):288-296, 1983.
Graham and Prevec, In: *Methods in Molecular Biology: Gene Transfer and Expression Protocol*, Murray (Ed.), Humana Press, Clifton, N.J., 7:109-128, 1991.
Graham and Prevec, *Mol. Biotechnol.*, 3(3):207-220, 1995.
Graham et al., *J. Gen. Virl.*, 36(1):59-74, 1977.
Graham, *J. Gen. Virol.*, 68(Pt 3):937-940, 1987.
Griffiths, *J. Histochem. Cytochem.*, 34(11):1389-1398, 1986.
Han et al., *Biol. Pharm. Bull.*, 22(8):83640, 1999.

Hermens and Verhaagen, *Prog. Neurobiol.*, 55(4):399-432, 1998.
Hollstein et al., *Science*, 253(5015):49-53, 1991.
Huyghe et al., *Human Gene Therapy*, 6:1403-1416, 1996.
Hurwitz et al., *Hum. Gene Ther.*, 10:441-48, 1999.
Irie et al., *Antisense Nucleic Acid Drug Dev.*, 9(4):341-9, 1999.
Ishibashi et al, *J. Clin. Invest.*, 92:883-893, 1993.
Ishibashi et al, *J. Clin. Invest.*, 93:1885-1893, 1994.
Jardon and Garnier, *Biotechnol Prog.*, 19(1):202-208, 2003.
Jiang et al., *Proc. Nat'l Acad. Sci. USA*, 93:9160-9165, 1996.
Jones and Shenk, *Cell*, 13:181-188, 1978.
Lesch, *Biol. Psychiatry*, 45(3):247-53, 1999.
Marienfeld et al., *Gene Ther.*, 6(6):1101-13, 1999.
McGrath et al., *J. Virol.*, 25:923-927, 1978.
Mincheff et al., *Eur. Urol.*, 38(2):208-17, 2000.
Mizrahi, *Dev. Biol. Stand.*, 55:219-230, 1983.
Morris et al., *Environ. Mol. Mutagen.*, 27(1):10-8, 1996.
Morrison et al., *J. Gen. Virol.*, 78(Pt 4):873-8, 1997.
O'Neil and Balkovic, *Biotechnology*, 11(2):173-178, 1993.
Parks et al., *J. Virol.*, 71(4):3293-8, 1997.
PCT Appl. WO 94/17178
PCT Appl. WO 98/00524
Perrin, *Vaccine*, 13(13):1244-1250, 1995.
Petrof, *Eur. Respir. J*, 11 (2):492-7, 1998.
Phillips et al., In:*Large Scale Mammalian Cell Culture* (Feder and Tolbert, eds.), Academic Press, FL, 1985.
Reddy et al., *Virology*, 251(2):414-26, 1998.
Robbins and Ghivizzani, *Pharmacol Ther*, 80(1):35-47, 1998.
Robbins et al., *Trends Biotechnol.*, 16(1):35-40, 1998.
Smith and Lee, *Anal Biochem.*, 86(1):252-263, 1978.
Stewart et al., *Gene Ther.*, 6(3):350-63, 1999.
Su et al., *Cancer Res.*, 58, 2339-2342, 1998.
Tanzawa et al, *FEBS Letters*, 118(1):81-84, 1980.
van Wezel, *Nature*, 216:64-65, 1967.
Vanderkwaak and Alvarez, *Curr. Opin. Obstet. Gynecol.*, 11(1):29-34, 1999.
Wagner et al., *Science*, 260:1510-1513, 1993.
Wang et al., In: *Animal Cell Technology: Basic and Applied Aspects*, Kaminogawa et al., (eds), 5:463-469, Kluwer Academic Publishers, Netherlands, 1993.
Wang et al., *Cytotechnology*, 9:41-49, 1992.
Wang et al., *Proc. Japan. Soc. Animal Cell Tech.*, 1994.
Watanabe, *Atherosclerosis*, 36:261-268, 1986.
Weinberg, *Science*, 254(5035):1138-1146, 1991.
Wilson, *J. Clin. Invest.*, 98(11):2435, 1996.
Wilson, *Nature*, 365:691-692, 1993.
Yotnda et al., *Gene Ther.*, 8:930-37, 2001.
Zheng et al., *J. Gen. Virol.*, 80(Pt 7):1735-42, 1999.

What is claimed is:

1. A method for producing an adenovirus, comprising:
   a) producing an adenovirus preparation in a bioreactor, comprising the steps of:
      (i) preparing a cell culture in the bioreactor by seeding the bioreactor with host cells and media;
      (ii) growing the host cells in the cell culture, comprising perfusing fresh media through the cell culture without the removal of cells from the bioreactor;
      (iii) initiating virus infection in the cell culture by diluting the cell culture with fresh media and adenovirus without the removal of cells from the bioreactor; and
   b) isolating adenovirus from the adenovirus preparation.

2. The method of claim 1, wherein the media is serum-free media.

3. The method of claim 1, wherein the media is protein-free media.

4. The method of claim 1, wherein the media is CD293.

5. The method of claim 1, wherein the bioreactor comprises a bioreactor that uses axial rocking of a planar platform to induce wave motions inside of the bioreactor.

6. The method of claim 5, wherein the wave motions are induced inside of a sterilized bag made of layers of polyethylene vinyl acetate and ethyl vinyl alcohol.

7. The method of claim 1, wherein the bioreactor is a disposable bioreactor.

8. The method of claim 1, wherein the bioreactor is a 10 L bioreactor.

9. The method of claim 1, wherein the bioreactor is a commercially-available bioreactor.

10. The method of claim 1, wherein preparing an adenovirus preparation further comprises monitoring pH of the media.

11. The method of claim 1, wherein preparing an adenovirus preparation further comprises monitoring dissolved oxygen tension in the media.

12. The method of claim 1, wherein preparing an adenovirus preparation further comprises monitoring temperature in the media.

13. The method of claim 1, wherein the media is perfused through a filter.

14. The method of claim 13, wherein the filter is internal to the bioreactor.

15. The method of claim 13, wherein the filter is external to the bioreactor.

16. The method of claim 13, wherein the filter is a floating flat filter.

17. The method of claim 13, wherein spent media is removed from the bioreactor through the filter.

18. The method of claim 1, wherein culture volume is maintained by a load cell used to trigger fresh medium addition.

19. The method of claim 1, wherein preparing an adenovirus preparation further comprises perfusing media beginning on day 3 of host cell growth.

20. The method of claim 1, wherein initiating virus infection is accomplished by diluting the host cells 2-fold to 50-fold with fresh media and adenovirus.

21. The method of claim 20, wherein the host cells are diluted 10-fold with fresh media and adenovirus.

22. The method of claim 1, wherein initiating virus infection comprises adding 20-100 vp/host cell.

23. The method of claim 22, wherein initiating virus infection comprises adding about 50 vp/host cell.

24. The method of claim 1, wherein preparing an adenovirus preparation further comprises allowing virus infection to proceed for about 4 days.

25. The method of claim 1, wherein isolating the adenovirus from the adenovirus preparation occurs at about 4 days after viral infection is completed.

26. The method of claim 1, wherein the adenovirus is a replication-deficient adenovirus.

27. The method of claim 26, wherein the host cells complement the growth of the replication-deficient adenovirus.

28. The method of claim 26, wherein the adenovirus lacks at least a portion of the E1-region.

29. The method of claim 26, wherein the adenovirus is lacking at least a portion of the E1A and/or E1B region.

30. The method of claim 1, wherein the host cells are selected from the group consisting of 293, PER.C6, 911, and IT293SF cells.

31. The method of claim 30, wherein the host cells are 293 cells.

32. The method of claim 1, wherein the adenovirus is a recombinant adenovirus.

33. The method of claim 32, wherein the recombinant adenovirus encodes a recombinant gene that is operatively linked to a promoter.

34. The method of claim 33, wherein the promoter is a tissue-specific promoter or an inducible promoter.

35. The method of claim 33, wherein the promoter is an SV40 EI, RSV LTR, beta-actin, CMV-IE, adenovirus major late, polyoma F9-1, tyrosinase promoter, alpha-fetal protein promoter, or egr-1.

36. The method of claim 33, wherein the recombinant gene is antisense ras, antisense myc, antisense raf, antisense erb, antisense src, antisense fins, antisense jun, antisense trk, antisense ret, antisense gsp, antisense hst, antisense bcl antisense abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, Rb, zac1, DBCCR-1, rks-3, COX-1, TFPI, PGS, Dp, E2F, ras, myc, neu, raferb, fins, trk, ret, gsp, hst, abl, E1A, p300, VEGF, FGF, thrombospondin, BAI-1, GDAIF, or MCC.

37. The method of claim 33, wherein the recombinant gene is a gene encoding an ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

38. The method of claim 33, where the recombinant gene is a gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione β-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, β-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, or human thymidine kinase.

39. The method of claim 33, wherein the recombinant gene encodes growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

40. The method of claim 33, wherein the recombinant gene is a p53 gene.

41. The method of claim 33, wherein the recombinant gene is a mda7 gene.

42. The method of claim 1, wherein isolating the adenovirus comprises lysing the host cells.

43. The method of claim 42, wherein lysing the host cells is by freeze-thaw, autolysis, or detergent lysis.

44. The method of claim 1, wherein isolating the adenovirus further comprises reducing the concentration of contaminating nucleic acids in the adenovirus preparation.

45. The method of claim 1, wherein isolating the adenovirus further comprises placing the adenovirus into a pharmaceutically acceptable composition.

46. The method of claim 1, wherein isolating the adenovirus further comprises purifying the adenovirus.

47. The method of claim 46, wherein purifying the adenovirus comprises a chromatography step.

48. The method of claim 47, wherein the chromatography step comprises subjecting the adenovirus to more than one chromatographic separation.

49. The method of claim 47, wherein the chromatography step involves subjecting the adenovirus to only one chromatographic separation.

50. The method of claim 49, wherein the chromatographic separation includes ion exchange chromatography.

51. The method of claim 1, further comprising analyzing virus production.

52. The method of claim 51, wherein virus production is analyzed using HPLC.

53. The method of claim 1, wherein isolating the adenovirus further comprises obtaining a purified adenovirus composition having one or more of the following properties:
 (a) a virus titer of between $1 \times 10^9$ and about $1 \times 10^{13}$ pfu/ml;
 (b) a virus particle concentration between about $1 \times 10^{10}$ and about $2 \times 10^{13}$ particles/ml;
 (c) a particle:pfu ratio between about 10 and about 60;
 (d) having less than 50 ng BSA per $1 \times 10^{12}$ viral particles;
 (e) between about 50 pg and 1 ng of contaminating human DNA per $1 \times 10^{12}$ viral particles;
 (f) a single HPLC elution peak consisting essentially of 97% to 99% of the area under the peak.

54. An adenovirus composition comprising between $5 \times 10^{14}$ and $1 \times 10^{18}$ viral particles, prepared by a process in accordance with claim 1.

55. The adenovirus composition of claim 54, wherein the composition is a pharmaceutically-acceptable composition.

56. The method of claim 1, wherein isolating the adenovirus from the adenovirus preparation comprises the steps of:
  (a) subjecting the adenovirus preparation to chromatography on a first chromatographic medium, whereby adenovirus particles are retained on the first chromatographic medium;
  (b) eluting adenovirus particles from the first chromatographic medium to produce an eluate of adenovirus particles;
  (c) subjecting adenovirus particles from the eluate to chromatography on a second chromatographic medium, wherein the second chromatographic medium retains one or more contaminants from the eluate and wherein the second chromotographic medium is not solely a size exclusion medium; and
  (d) collecting adenovirus particles from the eluate.

57. The method of claim 56, wherein the first chromatographic medium is selected from the group consisting of an anion exchange medium, cation exchange medium, immobilized metal affinity medium, sulfated affinity media, immunoaffinity medium, heparin affinity medium, hydroxyapatite medium, and hydrophobic interaction medium.

58. The method of claim 56, wherein the second chromatographic medium is selected from the group consisting of cation exchange media, anion exchange media, immobilized metal affinity media, sulfated affinity media, dye affinity media, hydroxyapatite media, immunoaffinity media, heparin affinity media, and hydrophobic interaction media.

59. The method of claim 1, wherein isolating the adenovirus from the adenovirus preparation comprises the steps of:
  (a) subjecting the adenovirus preparation to chromatography on a first chromatographic medium, whereby contaminants from the adenovirus preparation are retained on the first chromatographic medium;
  (b) subjecting adenovirus particles remaining in the eluant to chromatography on a second chromatographic medium whereby adenovirus particles from the eluant are retained on the second chromatographic medium, wherein when the second chromatographic medium is an anion exchange medium, then the first chromatographic medium is a medium other than a sulfonated polysaccharide affinity medium, and
  (c) eluting adenovirus particles from the second chromatographic medium.

60. The method of claim 59, wherein the first chromatographic medium is selected from the group consisting of an anion exchange medium, cation exchange medium, immobilized metal affinity medium, sulfated affinity media, immunoaffinity medium, heparin affinity medium, hydroxyapatite medium, and hydrophobic interaction medium.

61. The method of claim 59, wherein the second chromatographic medium is selected from the group consisting of cation exchange media, anion exchange media, immobilized metal affinity media, sulfated affinity media, dye affinity media, hydroxyapatite media, immunoaffinity media, heparin affinity media, and hydrophobic interaction media.

62. The method of claim 20, wherein initiating virus infection is accomplished by diluting the host cells 10-fold to 50-fold with fresh media and adenovirus.

\* \* \* \* \*

UNITED STATES PATENT AND TRADEMARK OFFICE
CERTIFICATE OF CORRECTION

PATENT NO. : 7,419,808 B2  Page 1 of 1
APPLICATION NO. : 11/079986
DATED : September 2, 2008
INVENTOR(S) : Shuyuan Zhang and Hai Pham It is certified that error appears in the above-identified patent and that said Letters Patent is hereby corrected as shown below:

In claim 36, column 49, line 14, delete "fins" and insert --fms-- therefor.

In claim 36, column 49, line 32, delete "raferb fins" and insert --raf erb fms-- therefor.

Signed and Sealed this

Eighteenth Day of November, 2008

JON W. DUDAS
*Director of the United States Patent and Trademark Office*